(12) United States Patent
Blagden

(10) Patent No.: US 12,352,751 B2
(45) Date of Patent: Jul. 8, 2025

(54) DETECTION OF LARP1

(71) Applicant: PRENOSTICS LIMITED, Oxfordshire (GB)

(72) Inventor: Sarah Blagden, Oxfordshire (GB)

(73) Assignee: Prenostics Limited

( * ) Notice: Subject to any disclaimer, the term of this patent is extended or adjusted under 35 U.S.C. 154(b) by 676 days.

(21) Appl. No.: 17/764,829

(22) PCT Filed: Sep. 29, 2020

(86) PCT No.: PCT/GB2020/052354
§ 371 (c)(1),
(2) Date: Mar. 29, 2022

(87) PCT Pub. No.: WO2021/064361
PCT Pub. Date: Apr. 8, 2021

(65) Prior Publication Data
US 2022/0326247 A1   Oct. 13, 2022

(30) Foreign Application Priority Data
Sep. 30, 2019   (GB) ...................................... 1914096

(51) Int. Cl.
*G01N 33/574*   (2006.01)
*G01N 33/68*   (2006.01)

(52) U.S. Cl.
CPC ... *G01N 33/57484* (2013.01); *G01N 33/6848* (2013.01); *G01N 2800/56* (2013.01)

(58) Field of Classification Search
CPC ............. C07K 5/1021; G01N 2800/52; G01N 2800/56; G01N 33/574; G01N 33/57415; G01N 33/57484; G01N 33/6848
See application file for complete search history.

(56) References Cited

U.S. PATENT DOCUMENTS

2005/0069491 A1*   3/2005   Szalay ................... A61P 35/00
424/9.6

FOREIGN PATENT DOCUMENTS

| WO | 2012/092302 A1 | 7/2012 |
| WO | 2016/075455 A1 | 5/2016 |

OTHER PUBLICATIONS

Anonymous: "Expasy PeptideMass performed on LARP-1 protein" Retrieved from the Internet: URL: <https://web.expasy.org/peptide_mass/,> 2 pages.
Castello. 2012, Insights into RNA biology from an atlas of mammalian mRNA-binding proteins, Cell, 149:1393-1406.

(Continued)

*Primary Examiner* — Jennifer Wecker
(74) *Attorney, Agent, or Firm* — Brown Rudnick LLP; Adam M. Schoen

(57) ABSTRACT

The invention relates to the detection of EGYR peptide in a biological sample as a measure of the presence and/or amount of LARP1 protein in the sample. Suitably, the invention relates to methods for quantitative measurement of LARP1 and LARP1-derived EGYR peptide by chromatography-tandem mass spectrometry. The invention also relates to peptide standards and their use in quantitative mass spectrometric analyses. The ability to detect the amount of LARP1 in a biological sample has application in detecting and monitoring cancer.

24 Claims, 4 Drawing Sheets

Specification includes a Sequence Listing.

(56) References Cited

OTHER PUBLICATIONS

Coosemans, 2017, P11.06 Could LARP1 be a driving force in ovarian cancer transformation?, 27th World Congress on Ultrasound in Obstetrics and Gynecology, vol. 50 (Suppl. 1), pp. 188-189.

Hopkins, 2015, The RNA-binding protein LARP1 is a post-transcriptional regulator of survival and tumorigenesis in ovarian cancer, Nucleic Acids Research, 44(3):1227-1246.

International Search Report and Written Opinion issued in International Application No. PCT/GB2020/052354, date of mailing: Jan. 12, 2021, 15 pages.

Xie, 2013, LARP1 predict the prognosis for early-stage and AFP-normal hepatocellular carcinom, Journal of Translational Medicine, 11(1):272, 10 pages.

Ye, 2016, Overexpression of LARP1 predicts poor prognosis of colorectal cancer and is expected to be a potential therapeutic target, Tumor Biology, 37(11):14585-14594.

Ghazaly, 2017, Abstract B30: The RNA-binding protein LARP1 is a cancer therapeutic target, Cancer Res, 77 (6_Supplement):B30, 4 pages.

The Promega website, "Protease Digestion for Mass Spectrometry", Retrieved from the internet on Apr. 13, 2023, URL:https://www.promega.co.uk/resources/guides/protein-analysis/protease-digestion-for-mass-spec/#, 18 pages.

* cited by examiner

DETECTION OF LARP1

RELATED APPLICATIONS

This application is a 35 U.S.C. 371 national stage entry of PCT/GB2020/052354, filed Sep. 29, 2020, which claims the benefit of, and priority to, GB Application 1914096.1, filed Sep. 30, 2019, the contents of each of which are incorporated by reference.

FIELD OF THE INVENTION

The invention relates to the detection of EGYR peptide in a biological sample as a measure of the presence and/or amount of LARP1 protein in the sample. In a particular aspect, the invention relates to methods for quantitative measurement of LARP1 and LARP1-derived EGYR peptide by chromatography-tandem mass spectrometry. The invention also relates to peptide standards and their use in quantitative mass spectrometric analyses.

BACKGROUND OF THE INVENTION

RNA binding proteins (RBPs) regulate the decay kinetics, translational efficiency and subcellular localisation of mRNA transcripts. In this way, the abundance and activity of mRNAs and their encoded proteins can be altered in a manner that is independent from gene transcription. As RBPs are themselves activated by growth factors and cell signals, this tightly-regulated post-transcriptional mechanism enables the cell to rapidly adjust levels of protein expression in response to intrinsic and extracellular signals. In addition, RBPs can interact with up to thousands of mRNA transcripts, allowing the coordinated synthesis of multiple proteins involved in a single physiological function (termed an RNA operon). However, when the expression of an RBP is disrupted it can potentially disrupt cellular homeostasis and autonomously drive pathological processes by uncoupling the regulation of mRNA stability from cell signalling cues. A protein identified as being an RBP is LARP1 (Castello et al Insights into RNA biology from an atlas of mammalian mRNA-binding proteins. Cell 149: 1393-1406). LARP1 belongs to the La-related protein (LARP) family and implicated in cancer. An elevated expression of LARP1 has been shown to correlate with clinical outcome in hepatocellular carcinoma (Xie et al., Journal of Translational Medicine 11: 272, 2013) and ovarian cancer (Hopkins et al., NAR, 2015). LARP1 was first identified in *Drosophila melanogaster*, where it was shown to bind poly(A)-binding protein (PABP) and was required for embryonic development and fertility. Proteomic screens conducted in human embryonic cell lines have subsequently shown that LARP1 interacts with 5'TOP mRNAs (those bearing 5' terminal oligopyrimidine (5'TOP) tracts) and contributes to their stability. 5TOP mRNAs are required for ribosome biogenesis and are regulated downstream of the mTOR (mammalian target of rapamycin) complex 1 (mTORC1) kinase and stress response proteins.

Human LARP1 consists of 1096 amino acids with an apparent molecular weight of about 150 kDa and a monoisotopic mass of 123434.17 g/mol.

WO2016/075455 teaches that LARP1 protein is a cancer biomarker which can be used to predict cancer progression or diagnosis and response to treatment. It discloses immunological detection such as enzyme-linked immunosorbent assay (ELISA). WO2016/075455 does not teach detection using mass spectrometry and particularly does not teach that LARP1 protein can be detected simply by detecting EGYR peptide.

When in the circulation, LARP1 is rapidly degraded and detecting LARP1 using Sandwich ELISA can be unpredictable as, due to protein fragmentation, levels of detection can change over time.

LARP1 is required for malignant transformation of cells. It attaches to mRNAs to stabilise them so that they can over-produce oncoproteins. This gives cells the ability to resist "stress" (e.g. chemotherapy or immunotherapy) and become more aggressive (tumour resilience).

Due to the difficulties in the current methods used to detect and quantify LARP1 in a biological sample, there is a need for improved methods of detecting LARP1 protein in biological samples, especially blood samples, including plasma and serum.

SUMMARY

Disclosed herein are methods for detecting LARP1 protein in a biological sample. In particular by using mass spectrometry to detect for the presence and/or the amount of the LARP1 peptide fragment with the amino acid sequence: EGYR (glutamic acid-glycine-tyrosine-arginine; or Glu-Gly-Tyr-Arg).

Although there are other proteins that contain EGYR peptide capable of being released as a tetrapeptide following trypsin digestion, the inventors have surprisingly discovered that LARP1 is released into the blood and can thus be detected in, for example plasma and serum. The other proteins that could release EGYR peptide following trypsin digestion are not believed to be present in the blood, or only at fixed/constitutive levels which would be accommodated by background control values.

Examples of human proteins which could, on cleavage with trypsin, release EGYR peptide include: Nebulin, PHD finger protein 13, RING finger and CHY zinc finger domain-containing protein 1, & YaeI domain-containing protein 1. These proteins include the pentapeptide KEGYR and would thus be expected to release EGYR after trypsin digestion.

In addition, proteins containing a related REGYR motif may also release the EGYR peptide after trypsin digestion. There are also 4 of these in the human proteome according to SwissProt. These are: CCP module-containing protein 22, Complement C5 beta chain, L-2-hydroxyglutarate dehydrogenase, mitochondrial, & Fibroblast growth factor 16.

In circumstances where it is known that a further protein capable of releasing EGYR peptide after trypsin digestion is present in the test sample, the amount of this protein in the sample can be calculated by detecting for a peptide that is present in this protein but not within LARP1 and then deducting the relative amount of this protein from the total amount of EGYR detected in the sample. In this way the test can accurately determine the amount of LARP1 protein in the sample.

Thus, according to the first aspect of the invention there is provided a method for detecting LARP-1 protein in a biological sample, comprising producing a protein digest from the biological sample; and detecting for the presence of EGYR fragment peptide in the protein digest, thereby determining the presence of LARP-1 in the biological sample.

In one embodiment, the method includes obtaining a biological sample from a subject. Suitably, the subject is a mammal such as a human.

In another embodiment, the biological sample is digested with a protein cleavage agent (such as a serine protease, for example trypsin). The digested sample (protein digest) is optionally subjected to chromatographic separation prior to detecting for a LARP1 fragment peptide with the amino acid sequence: EGYR, using mass spectrometry. In a particular embodiment, the biological sample is subjected to protein digestion, chromatography and tandem mass spectrometry in order to determine the presence and optionally the amount of EGYR peptide in the biological sample (test sample).

In a particular embodiment, the methods of the invention include subjecting the sample to proteolytic degradation or cleavage followed by ionization under conditions suitable to produce charged EGYR-derived peptide ions detectable by mass spectrometry; determining by mass spectrometry the amount of one or more ions from the one or more EGYR-derived peptides; and using the amount of the determined ions to determine the presence or and/or amount of LARP1 protein in the sample. Optionally, the sample of proteolytically degraded or cleaved proteins is subjected to chromatography to separate out the various cleaved proteins and the fraction that comprises peptides with the EGYR amino acid sequence is then subjected to the mass spectrometry.

The presence of the EGYR peptide in the protein digest indicates the presence of LARP1 protein in the sample. LARP1 is a cancer biomarker and so this method facilitates testing for and monitoring this cancer biomarker. In some embodiments, the LARP1-derived EGYR fragment peptide is detected by mass spectrometry. In some embodiments, the LARP1-derived EGYR fragment peptide is detected by the detection of fragment ions of the EGYR fragment peptide, for example using tandem mass spectrometry.

Also disclosed are methods of quantitating the amount of the EGYR fragment peptide in a biological sample. In one embodiment, such methods include comparing an amount of the EGYR fragment peptide in the test sample to an optionally isotopically labelled EGYR peptide standard of known amount. Peptide standards for use in quantitating LARP1-derived EGYR peptide in a biological sample are also disclosed. Such peptide standards consist of or comprises the EGYR amino acids and are optionally isotopically labelled. A standard curve can be generated using known spiked amounts of recombinant LARP1, or a LARP-1 peptide (e.g. EGYR peptide). This can then be used to determine what peptide intensity corresponds to what amount of LARP1.

The ability to detect the presence of and quantify the amount of LARP1 protein or EGYR peptide in a sample has numerous applications.

In one application, the disclosed methods can be used to determine the progression of a cancer in a patient by correlating the detected amount of the EGYR fragment peptide over time to progression of the cancer. In addition, the disclosed methods can be used to monitor the efficacy of a treatment by determining the change in the amount of LARP1 protein in the biological sample following treatment, suitably the biological sample is a blood sample or blood-derived sample such as plasma or serum. By way of example, the presence of an EGYR fragment peptide in the protein digest indicates that the subject expresses high levels of LARP1 protein which is indicative of burden or activity of cancer within their body.

According to a second aspect of the invention there is provided a method for determining the amount of LARP-1 protein in a sample, comprising:
(a) subjecting the sample to trypsin digestion, followed by ionisation under conditions suitable to produce positively charged EGYR peptide ions detectable by mass spectrometry;
(b) determining by mass spectrometry the amount of charged ions produced in (a); and
(c) using the determined amount of ions in step (b) to determine the amount of LARP-1 protein in the sample.

Suitably, step (c) is carried out using a standard curve.

By trypsin digestion we mean contacting the sample with trypsin or a trypsin variant capable of cleaving the proteins after arginine and/or lysine residues.

Optionally, the sample is treated before step (a) to fragment or cleave the proteins in the sample and/or is subjected to chromatography.

Detecting the amount of ion in MS is suitably done by comparison to a standard curve (e.g. on generated in a control sample by spiking in known amounts of recombinant LARP1), and determine what peptide intensity corresponds to what amount of LARP1.

The ions, e.g. protonated ions, generated by electrospray or MALDI would be positively charged EGYR peptide ions. In these types of MS analyses (known as selective reaction monitoring or SRM), a positive detection typically also requires fragmentation and matching of 1 or 2 of the diagnostic fragment ions. Accordingly, in addition to the original non-fragmented EGYR ion, one or two fragment ions of this peptide in the MS/MS could be detected.

According to a third aspect of the invention there is provided a method for prognosing the development of cancer, comprising
(a) treating a biological sample from a patient with trypsin or trypsin variant;
(b) subjecting the treated sample to mass spectrometry;
(c) determining by mass spectrometry the amount of ionised EGYR peptide; and
(d) using said amount determined in (c) to determine the amount of EGYR peptide in the treated sample, wherein elevated levels of EGYR peptide in the treated sample relative to normal or control levels indicates a poorer prognosis with respect to the development of cancer.

The trypsin or trypsin variant serve to cleave the proteins in the sample after arginine and lysine residues. Suitably in step (a) the proteins in the biological sample are cleaved by the trypsin or trypsin variant after arginine and lysine residues.

Suitably in step (b) the sample is treated to ionisation under conditions suitable to produce one or more charged ions detectable by mass spectrometry.

According to a fourth aspect of the invention there is a method of determining whether a cancer patient responds to a therapeutic treatment, comprising detecting the level of LARP1 protein in a biological sample from the patient after the therapeutic treatment; and comparing the level of LARP1 protein in said sample with the level of LARP1 protein in a control sample, wherein the detecting comprises mass spectrometry and wherein an elevated level of LARP1 protein in said sample from said subject compared to the level of LARP1 protein in said control sample indicates that the subject does not respond to said therapeutic treatment.

According to a fifth aspect of the invention there is a method of identifying subjects that are in early stages of cancer development comprising detecting the level of LARP1 protein in a serum or plasma sample from the subject; and comparing the level of LARP1 protein in said sample with the level of LARP1 protein with an age-matched reference value or in a control sample, wherein an elevated level of LARP1 protein in said sample from said subject compared to the level of LARP1 protein in said reference value of in the control sample indicates that the subject is in early stages of cancer development.

According to a sixth aspect of the invention there is a method of predicting the presence of serous tubal intraepithelial carcinoma (STIC) in a subject comprising detecting the level of LARP1 protein in a serum or plasma sample from the subject; and comparing the level of LARP1 protein in said sample with a reference value of LARP1 protein or with the level of LARP1 in a control sample, wherein an elevated level of LARP1 protein in said sample from said subject compared to the reference value or the level of LARP1 protein in the control sample predicts that the subject has STIC.

According to a seventh aspect of the invention there is a method for diagnosing or predicting risk of developing cancer, comprising subjecting a biological sample obtained from a patient to one or more processing steps to cleave the proteins in the sample to smaller peptides, wherein if LARP1 protein is in the sample the peptides produced include EGYR peptide; subjecting the processed sample to ionization under conditions suitable to produce one or more multiply charged ions detectable by mass spectrometry; determining by mass spectrometry the amount of one or more ions from the LARP1-derived EGYR peptide; and using the determined ion amounts to determine the amount of LARP1 protein in the biological sample or EGYR peptide in the processed sample, wherein an elevated LARP1 protein level in the biological sample relative to normal indicates the presence of or risk of developing cancer.

According to a eighth aspect of the invention there is a method for determining the amount of LARP-1 protein in a biological sample, comprising:
(a) treating the biological sample with trypsin or trypsin variant to cleave the proteins in the sample;
(b) subjecting the treated sample to ionisation under conditions suitable to produce charged EGYR peptide ions detectable by mass spectrometry;
(c) detecting the charged ions produced in (b); and
(d) using the amount of ions in step (c) to determine the amount of LARP-1 protein in the sample.

Suitably, the sample subjected to mass spectrometry is spiked with an internal standard so that the amount of EGYR-derived protein, e.g. LARP1 can be quantitated.

According to a ninth aspect of the invention there is provided an isolated peptide comprising the amino acid sequence EGYR. Such a peptide may be referred to as a peptide standard. In one embodiment the peptide consists of the amino acid sequence EGYR. In particular embodiments, the peptide is labelled. Suitably the peptide is fluorescently labelled or is isotopically labelled. In particular embodiments, the EGYR peptide is labelled with an isotope selected from: deuterium ($^2$H), $^{13}$C, $^{15}$N, $^{35}$S, $^{17}$O and $^{18}$O.

A particular isotopically labelled EGYR peptide has a m/z of about 534.2.

The summary of the invention described above is non-limiting and other features and advantages of the invention will be apparent from the following detailed description of the invention, and from the claims.

The methods according to the first to eighth aspects of the invention are particularly suited for use on a subject with cancer or suspected of having cancer. They are also particularly suited for use on a subject with an increased susceptibility to developing cancer; such as, a patient with BRCA1 or BRCA2 or other driver mutations in their genomic DNA.

DETAILED DESCRIPTION OF THE INVENTION

Figure 1:
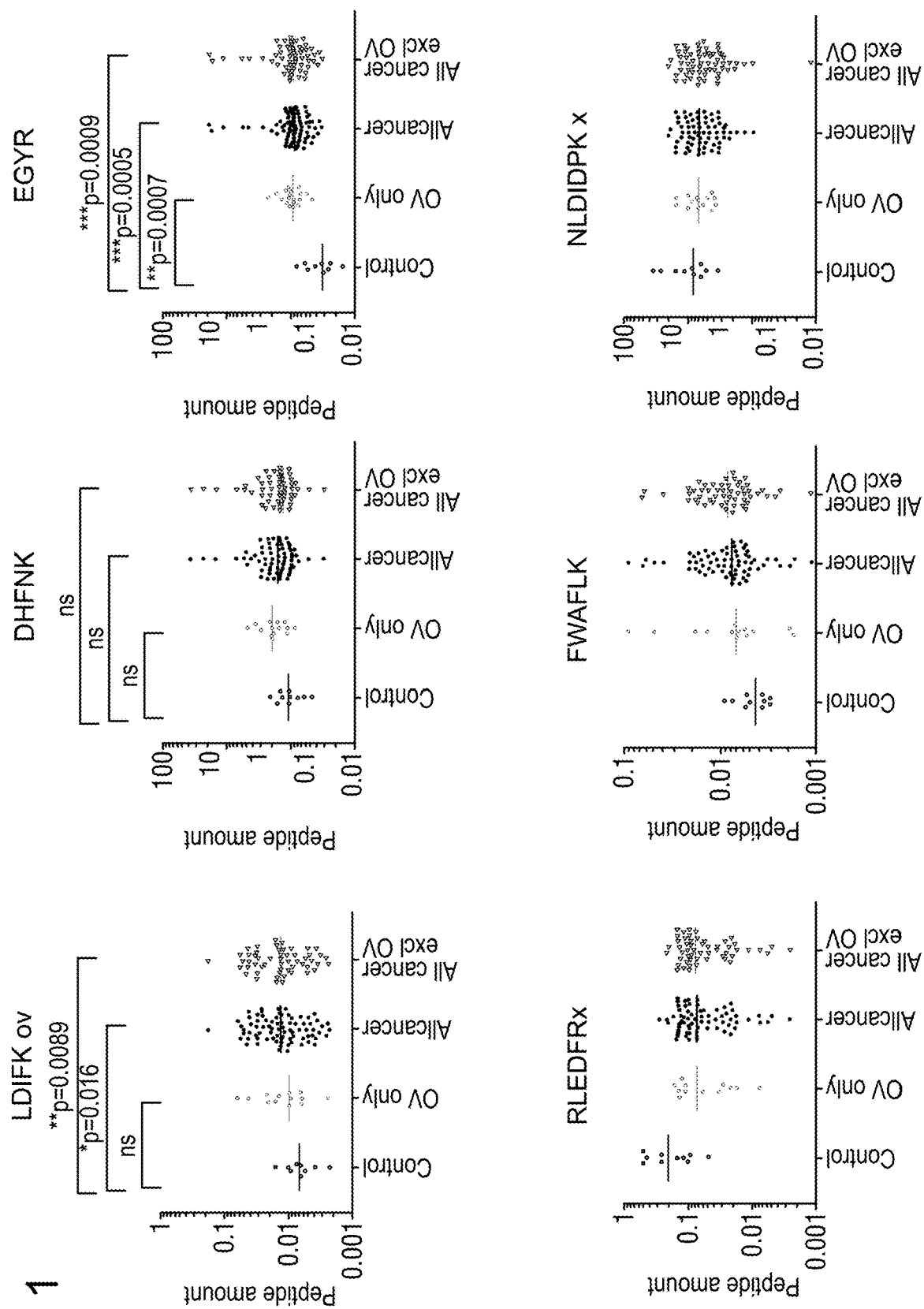
FIG. 1 Correlation of the 6 different LARP1 peptide sequences detectable by MS with disease state in plasma collected from patients with advanced cancers.
Figure 2A:
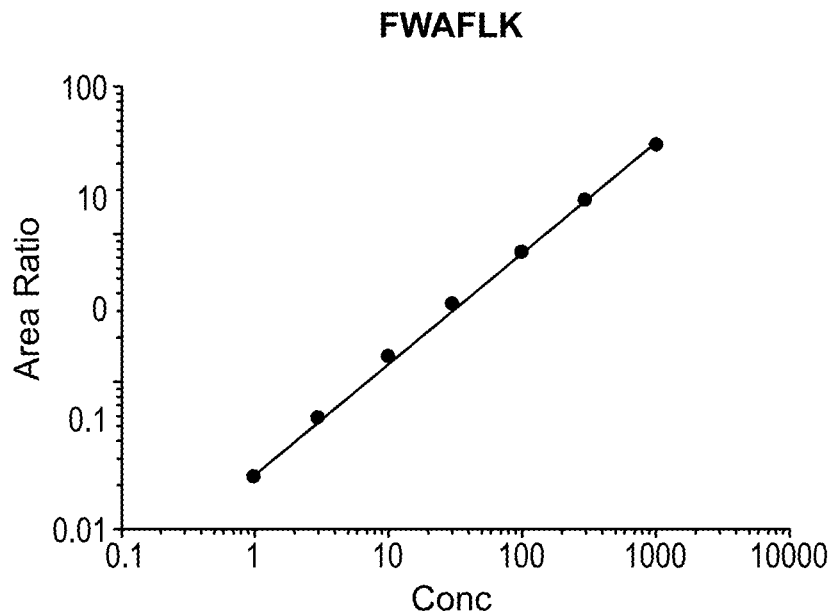
FIG. 2: Example of optimising a LARP1 peptide sequence
A) Calibration curve for peptide sequence 4 (FWAFLK) showing the peptide concentration (ng/ml) plotted against the area ratio (peptide area/labelled internal standard area).
B) Calibration standard for LARP1 (1000 ng/ml) FWAFLK peptide sequence 4 with peak eluting at 12.5 (upper panel) and labelled internal standard eluting at the same time (lower panel).
C) Untreated mice plasma sample with absent peptide peak at 12.5 minute (upper panel) and labelled internal standard eluting at the same time (lower panel).
D) Mice plasma extracted after 4 weeks of inoculation of $5\times10^6$ of ovarian tumor cells showing LARP1 FWAFLK peptide sequence 4 with peak eluting at 12.5 (corresponding to a concentration of 121 ng/ml).
Figure 2B:
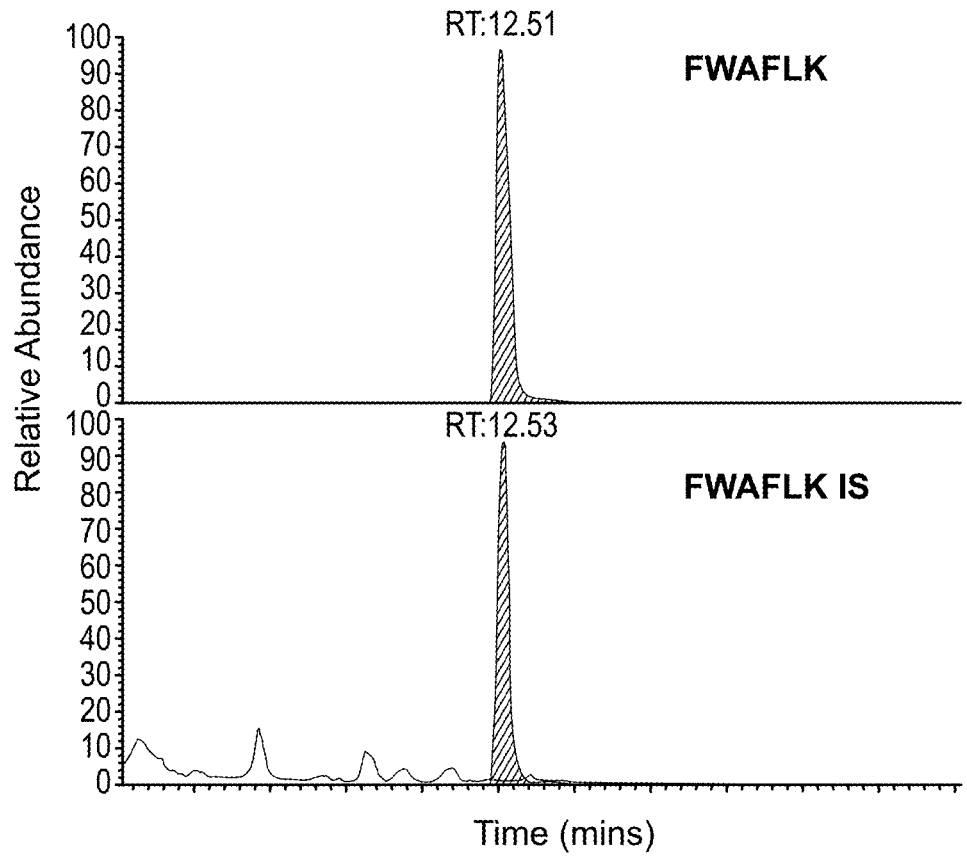
Figure 2C:
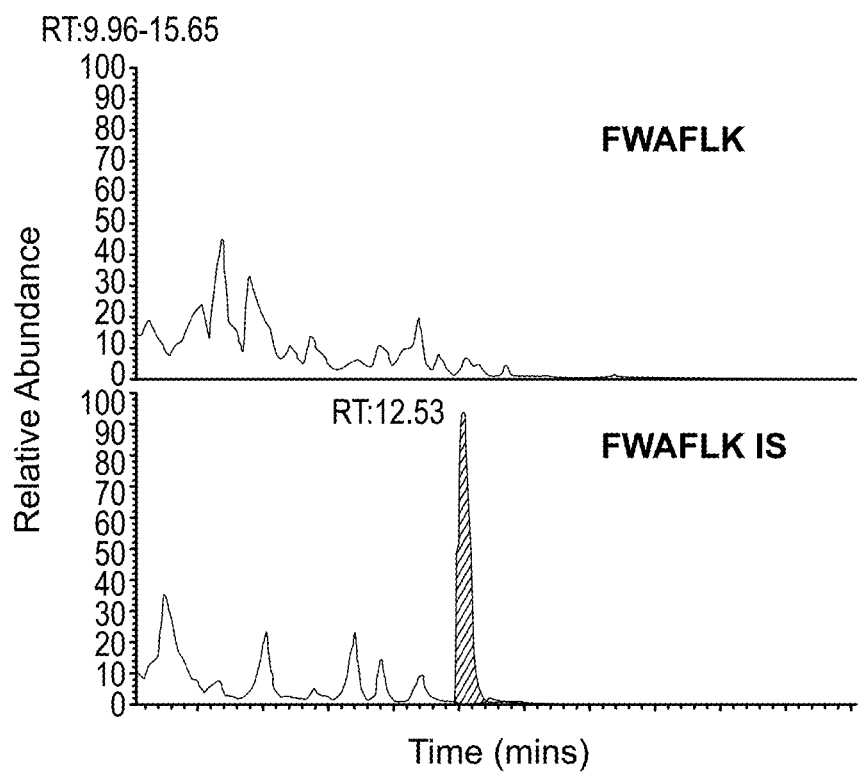
Figure 2D:
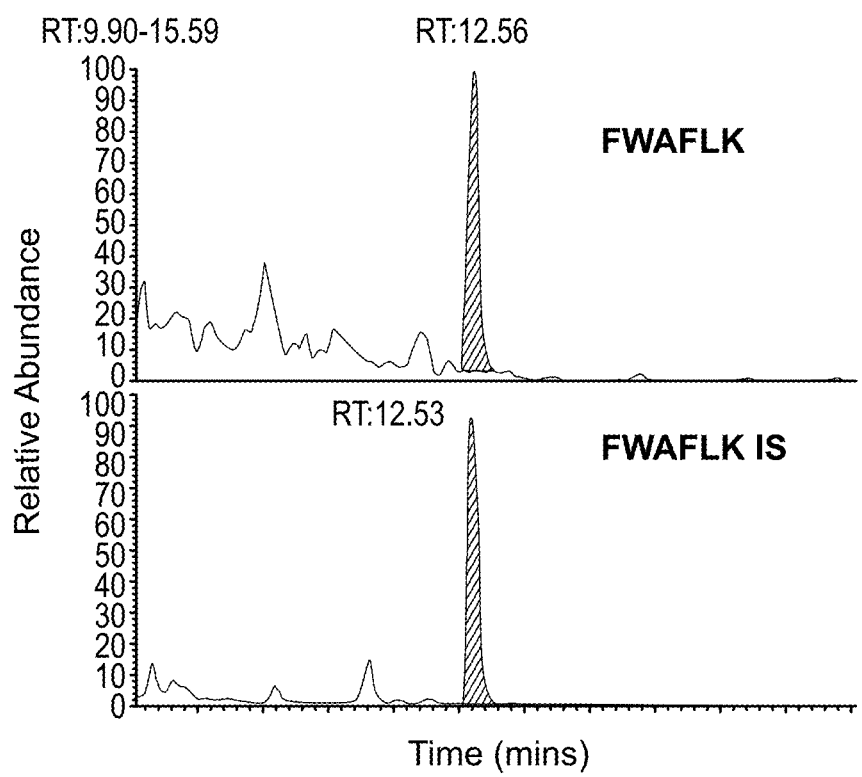
Figure 3:
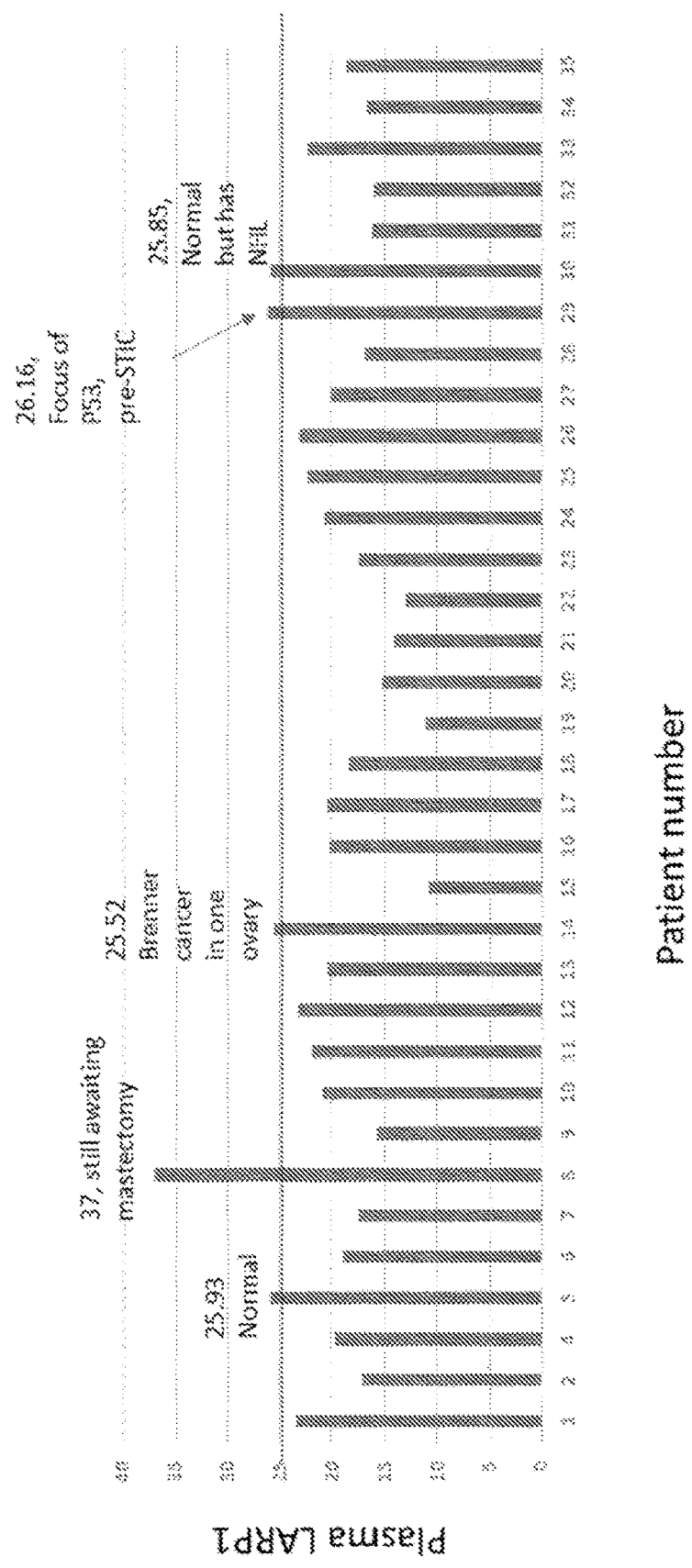
FIG. 3: Correlation between levels of plasma LARP1 and diagnosis in women with hereditary cancer syndromes (mainly BRCA mutation carriers) prior to prophylactic risk-reducing surgery.

As used herein, unless otherwise stated, the singular forms "a," "an," and "the" include plural reference. Thus, for example, a reference to "a protein" includes a plurality of protein molecules. Similarly, the word "or" is intended to include "and" unless the context clearly indicates otherwise.

The following definitions may be useful in the understanding of the invention.

As used herein, the term "LARP1" means LARP1 protein. There are at least 7 putative LARP1 mRNA transcript variants. Variant 1 (NM_015315.5) encoding the 1019 amino protein NP_056130.2, isoform 1; Variant 2 (NM_033551.5) encoding the 1096 amino acid protein NP_291029.2, isoform 2; Variants 3,4,9 (NM_1367713, NM_1367714.1 and NM_1367719.1) encoding the 891 amino acid proteins NP_1354642, NP_1354643.1 and NP_1354648.1, all known as isoform 3; Variant 5 (NM_1367715.1) encoding the 824 amino acid protein NP_135464.1, isoform 4; Variant 6 (NM_1367716.1) encoding the 858 amino acid protein NP_1354645.1, isoform 5; Variant 7 (NM_1367717.1) encoding the 993 amino acid protein NP_NP_1354646.1, isoform 6; and Variant 8 (NM_1367718.1) encoding the 1063 amino acid protein NP_1354647.1, isoform 7. The nucleotide sequence of a representative LARP1 mRNA (variant 1) is disclosed in SEQ ID NO: 1. The amino acid sequences of LARP1 variant 1 isoform is shown in SEQ ID NO: 2.

As used herein, the term "LARP1-derived EGYR peptide" refers to the peptide or group of peptides that comprise the amino acid sequence EGYR (glutamic acid-glycine-tyrosine-arginine) which is found within the amino acid sequence of LARP1 protein. Such peptide may be 4 amino acids in length, or could be longer, possessing additional amino acids at the C- and/or N-terminus of the peptide due to trypsin mis-cleavage. Typically, such peptide will be up to 12 amino acids in length; trypsin mis-cleavage of LARP1 is predicted to produce a peptide that is either 11 or 12 amino acids long. In a particular embodiment, the LARP1-derived EGYR peptide fragment has or consists of the amino acid sequence EGYR.

As used herein, the term "isolated" as applied to a polypeptide means a polypeptide that has been separated from components that naturally accompany it. Typically, the polypeptide is substantially isolated when it is at least 70%, by weight, free from other proteins and naturally occurring organic molecules with which it is naturally associated. Suitably, the polypeptide is at least 75%, such as at least 80%, at least 90% at least 95%, at least 99% or 100%, by weight, isolated. An isolated polypeptide may be obtained by standard techniques, for example, by extraction from a natural source (e.g., purification from a cell or body fluid). The percent of isolation can also be a measure of purity. Purity can be measured by any appropriate method, e.g., by column chromatography, polyacrylamide gel electrophoresis, or HPLC analysis.

As used herein, the term "about" in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.5 atomic mass unit (amu), such as +/−0.3 atomic mass unit, +/−0.2 atomic mass unit or +/−0.1 atomic mass unit.

As used herein, the term "purification" or "purifying" refers to a process that enriches the amount of one or more analytes of interest (e.g. peptides or polypeptides) relative to other components in the sample that may interfere with detection of the analyte of interest.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In some embodiments, the sample comprises a body fluid sample from a patient; suitably this can be plasma or serum.

Serum is the liquid fraction of the blood that remains when a whole blood sample is allowed to clot. Accordingly, serum is obtained by allowing the whole blood sample to clot. This can be done, for example, by leaving the sample undisturbed at room temperature for around 15-30 minutes. The serum can be obtained by removing the clot, for example by centrifuging the sample. This can be done, for example, at 1,000-2,000×g for 10 minutes in a refrigerated centrifuge. The resulting supernatant is serum.

Plasma is produced when whole blood is treated with an anticoagulant. This can be done, for example, by collecting blood in tubes that are treated with an anticoagulant. Plasma can then be obtained by centrifugation. This can be done, for example, at 1,000-2,000×g for 10 minutes in a refrigerated centrifuge. The resulting supernatant is plasma.

As used herein, the term "solid phase extraction" or "SPE" refers to a sample preparation process in which compounds which are dissolved or suspended in a liquid mixture are separated from other compounds in the mixture according to their physical and chemical properties. SPE uses the affinity of solutes dissolved or suspended in a liquid (known as the mobile phase) for a solid through which the sample is passed (known as the stationary phase) to separate a mixture into desired and undesired components. In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis.

As used herein, the term "chromatography" refers to a process in which a mixture of chemicals within a liquid or gas is separated into components as they pass around or over a stationary liquid or solid phase. Examples of methods of chromatographic separation include capillary-action chromatography such as paper chromatography, gel chromatography such as gel filtration chromatography, thin layer chromatography (TLC), column chromatography, fast protein liquid chromatography (FPLC), size exclusion chromatography, ion exchange chromatography, affinity chromatography, high performance liquid chromatography (HPLC), and reverse phase high performance liquid chromatography (RP-HPLC) amongst others.

As used herein, the term "liquid chromatography" or "LC" refers to a process of passing a mixture of particles (ions, compounds, peptide molecules etc) to be separated through a column filled with a packing material of a finely divided substance known as the stationary phase. The separation arises from differences in adsorption, size, charge etc of the individual ions or molecules as the fluid moves relative to the stationary phase(s). Examples of "liquid chromatography" include normal phase liquid chromatography (NPLC), reverse phase liquid chromatography (RPLC), high performance liquid chromatography (HPLC) and ultra high performance liquid chromatography (UHPLC).

As used herein, the term "high performance liquid chromatography" or "HPLC" (sometimes known as "high pressure liquid chromatography") refers to liquid chromatography in which the mobile phase is forced under pressure through a stationary phase, typically a densely packed column. HPLC instruments use a pump to force the mobile phase through and provide higher resolution and faster analysis time.

As used herein, the term "ultra high performance liquid chromatography" or "UHPLC" (sometimes known as "ultra high pressure liquid chromatography") refers to a form of column chromatography used to separate, identify, and quantify compounds. It allows for separation and analysis of small particles both quickly and effectively. With UHPLC the mobile phase is forced under high pressure through a stationary phase, typically a densely packed column with a stationary phase comprising packing particles that have an average diameter of than 2 μM. As the mobile phase is passing through the stationary phase a detector shows the retention times of the different molecules. Retention time varies depending on the interactions between the stationary phase, the molecules being analyzed, and the solvent used.

As used herein, the term "gas chromatography" or "GC" refers to a type of chromatography for analysing compounds that can be vaporized without decomposition. The sample mixture is vaporized and injected into a stream of carrier gas (such as nitrogen or helium) moving through a column containing a stationary phase composed of a liquid or, for example a particulate solid if in a packed column, and is separated into its component compounds according to the affinity of the compounds for the stationary phase.

As used herein, the term "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 μm in diameter.

As used herein, the term "on-line" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. Typically, a sample is analysed by generating gas phase ions from the sample, which are then separated according to their mass-to-charge ratio (m/z) and detected. MS technology generally includes (1) ionizing the compounds to form charged compounds; (2) calculating a mass-to-charge ratio (m/z). and (3) detecting the molecular weight of the charged compounds; The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z").

Methods of generating gas phase ions from a sample include electrospray ionization (ESI), matrix-assisted laser desorption-ionization (MALDI), surface-enhanced laser desorption-ionization (SELDI) and chemical ionization. Separation of ions according to their m/z ratio can be accomplished with any type of mass analyser, including quadrupole mass analysers (Q), time-of-flight (TOF) mass analysers, magnetic sector mass analysers, 3D and linear ion traps (IT), Fourier-transform ion cyclotron resonance (FT-ICR) analysers, and combinations thereof (for example, a quadrupole-time-of-flight analyser, or Q-TOF analyser). Prior to ionisation, the sample may be subjected to one or more dimensions of chromatographic separation, for example, one or more dimensions of liquid or size exclusion chromatography.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to an ionization technique that uses a laser energy absorbing matrix to create ions from large molecules with minimal fragmentation. MALDI methodology is a three-step process. First, the sample is mixed with a suitable matrix material and applied to a metal plate. Second, a pulsed laser irradiates the sample and thirdly, the analyte molecules are ionized by being protonated ($H^+$ addition) or deprotonated ($H^+$ removal) in the hot plume of ablated gases. They can then be accelerated into whichever mass spectrometer is used to analyse them As used herein, the term "surface enhanced laser desorption ionization" or "SELDI" refers to an ionization method suitable for analysis of protein mixtures in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface before MS analysis.

As used herein, the term "electrospray ionization" or "ESI," refers to methods in which a high voltage is applied to a liquid to create an aerosol of very small droplets of solution in solvent vapor. This mist of droplets flows through an evaporation chamber. As the droplets get smaller the electrical surface charge density increases until such time that the natural repulsion between like charges causes ions as well as neutral molecules to be released. ESI is different from other ionization methods in that it may produce multiple-charged ions, effectively extending the mass range of the analyser. Heated ESI is similar but includes a heat source for heating the sample while in the capillary tube. Mass spectrometry using ESI is called electrospray ionization mass spectrometry (ESI-MS).

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" or "SIM" is a detection mode for a mass spectrometric instrument in which only ions within a relatively narrow mass range, typically about one mass unit, are detected.

As used herein, "selected reaction monitoring" or "SRM" is a detection mode for a mass spectrometric instrument in which a precursor ion and one or more fragment ions are selectively detected.

As used herein, the term "prognosis" refers to the likely outcome of a disease process or event. For example, the prognosis of a subject with cancer can indicate the likelihood that the subject will survive for a period of time (e.g. 5 years) and/or will enter remission and/or the likelihood of metastasis. The prognosis of a subject with cancer can also indicate the likelihood that the subject will remain disease-free following treatment for a period of time (e.g. 5 years).

As used herein, the terms "diagnosis" or "medical diagnosis" refer to the identification of the nature and cause of a certain phenomenon, such as a disease or medical condition. Diagnosis is the process of determining which disease or condition explains an individual's symptoms and signs. A diagnosis is the classification of an individual's condition into separate and distinct categories that allow medical decisions regarding treatment and prognosis to be made.

As used herein, the term "cancer" refers to a disease caused by an uncontrolled division of abnormal cells in a part of the body which can then invade nearby tissues and spread to other parts of the body.

"Pre-cancerous conditions". Cancer is frequently preceded by the development of a pre-cancerous condition, which is not itself cancerous, but is associated with an increased risk of cancer. Examples of pre-cancerous conditions include, but are not limited to, those selected from the group consisting of: actinic keratosis, Barrett's oesophagus, atrophic gastritis, dyskeratosis congenital, Sideropenic dysphagia, Lichen planus, oral submucous fibrosis, solar elastosis, cervical dysplasia, leukoplakia, erythroplakia, monoclonal gammopathy of unknown significance (MGUS), monoclonal B-cell lymphocytosis (MBL), myelodysplastic syndromes, as well as pre-cancerous conditions of the stomach such as atrophic gastritis, gastric ulcer, pernicious anaemia, gastric stumps, gastric polyps, and Menetrier's disease. Among the listed pre-cancerous conditions of the stomach, atrophic gastritis, pernicious anaemia, gastric stumps, and certain types of gastric polyp may have particularly heightened risk of developing into cancers. Also Precancerous pancreatic, breast, cervix and prostate lesions, called cancers "in situ" or Stage 0, or PDAC (pancreatic ductal carcinoma in situ), DCIS (ductal carcinoma in situ), CIN (cervical intra-epithelial neoplasia), PIN (prostatic intraepithelial neoplasia).

Pre-cancerous conditions often take the form of lesions comprising dysplastic or hyperplastic cells. The severity of dysplasia can vary between different pre-cancerous conditions, or with the development of a single pre-cancerous condition over time. Generally, the more advanced dysplasia associated with a pre-cancerous condition is, the more likely it is that the pre-cancerous condition will to develop into cancer. Dysplasia is typically classified as mild, moderate or severe. Severe dysplasia usually develops into cancer if left untreated.

As used herein, the term "cancer-predisposing mutations" or "driver mutations" refers to particular mutations or polymorphic forms within the nucleic acid of certain genes whose presence are associated with an increased risk of developing a cancer. Examples of genes that are recognised as being capable of possessing one or more cancer-predisposing mutations in certain patients include: BRCA1, BRCA2, KRAS, P53, ALK and HER2.

Detection of EGYR Peptide in Biological Samples

Methods are described for detecting and/or quantifying the amount of EGYR peptide (which may be derived from LARP1 protein) in a sample. More specifically, mass spectrometric methods are described for detecting and quantifying the EGYR peptide in a sample. The methods may utilize solid phase extraction and/or liquid chromatography, to perform a purification of selected analytes (e.g. EGYR peptide), combined with methods of mass spectrometry (MS), thereby providing a high-throughput assay system for detecting and quantifying EGYR peptide in a sample. The methods are particularly well suited for application in large clinical laboratories for automated EGYR peptide quantification.

According to a first aspect of the invention there is provided a method for detecting LARP-1 protein in a sample, comprising producing a protein digest from the sample; and detecting for the presence of EGYR fragment peptide in the protein digest, thereby determining the presence of LARP-1 in the sample. Suitably the sample is a biological sample. The method may include the step of obtaining a biological sample from a subject or it may be practised on a sample already isolated/obtained from a patient.

In one embodiment, the method includes obtaining a biological sample from a subject or individual. The subject or individual may be a mammal. The subject or individual may be a human. In another embodiment, the biological sample is from a patient with or suspected of having cancer or a pre-cancer.

The methods of the invention are typically carried out on a sample that has previously been obtained from a patient/subject. Thus, the taking of the sample does not typically form part of the methods of the invention and the methods of the invention are carried out on a sample that has been obtained from a subject. In some embodiments of the invention, however, the method also comprises taking the sample from the subject, for example by taking a blood sample.

Suitable test samples for use in the methods of the present invention include any sample that may contain the LARP1 protein (the analyte) of interest. In some embodiments, a sample is a biological sample; that is, any solid or fluid sample obtained from any living organism, including without limitation, a multicellular organism such as an animal, including samples from a healthy or apparently healthy human subject or a human patient affected by a condition or disease to be diagnosed or investigated, such as cancer.

The sample can be from a mammalian animal, such as a dog, cat, horse, etc. Suitably the mammalian animals are primates, and in particular, are male or female humans.

The methods of the invention are particularly suited to testing liquid biological samples. In particular embodiments, the biological sample is selected from the group consisting of: a blood sample, a plasma sample, a serum sample, a urine sample, a cerebrospinal fluid, an ascites sample and a saliva sample. Such samples may be obtained, for example, from a patient with or suspected of having a disease or condition.

The inventors have found that plasma samples yield optimal results and so in a particular embodiment, the biological sample used in the methods of the invention is a plasma sample.

In particular embodiments, the methods of the invention may be used to determine the amount of LARP1 protein in a biological sample obtained from a subject/patient, or the amount of LARP1-derived EGYR peptide in a processed sample from a subject/patient.

If it is known that the only variable EGYR containing protein in the sample is LARP1 then quantitation of the amount of LARP1 in the sample can be used to directly determine the amount of LAPR1 present. By "variable EGYR containing protein" we mean that the amount of the protein that comprises the cleavage derivable EGYR peptide fluctuates. If it does not fluctuate and the amount in a control sample is likely to be stable or predictable then the amount of EGYR peptide from a non-LARP1 protein can be easily discounted or subtratcted to yield the amount of LARP1 derived EGYR peptide in the sample. If the biological sample contains one or more variable EGYR containing proteins then the amount of LARP1 protein in the sample can be determined by detecting the amount of one or more other peptides that are indicative of LARP1 (such as those disclosed in SEQ ID Nos 4-9) or the other EGYR containing proteins in order to accurately determine the amount of LARP1 in the sample.

As used herein, unless the context dictates otherwise, reference to the sample refers to the sample obtained from the patient/subject or such a sample that has been subjected to subsequent processing, such as proteolytic digestion, purification, etc.

Sample Preparation

The sample should be treated so as to digest or cleave the proteins in the biological sample (including LARP1 protein) so as to facilitate the generation of the EGYR peptide. The sample may thus be subjected to one or more processing steps prior to detection for EGYR peptide. Examples of processing steps include: protein fragmentation (e.g. digestion, cleavage or degradation) and purification. The most appropriate means is cleavage of the protein using a proteolytic enzyme, such as one that can cleave after arginine and lysine residues; The most suitable enzyme for effecting this is trypsin, or a typsin variant/analogue.

Protein Cleavage

In some embodiments, the sample is processed to convert the proteins into smaller peptide fragments. Internal standard may be added to the samples prior or subsequent to cleavage.

This fragmentation can be effected by shearing forces, such as generated by passing the sample through a narrow bore syringe or following sonication. However, the fragmentation is preferably performed using one or more proteases capable of digesting the proteins in the sample into smaller peptides. Trypsin or its variants are particularly suitable.

Optionally, prior to enzymatic cleavage, the biological sample can be subjected to physical shearing by sonication or by passing the sample through a small-bore syringe such as a G23 syringe, one or more times. In particular embodiments the protein is prepared by sonication or passing the sample through a narrow bore aperture, such as a syringe.

As used herein a peptide is a short chain of 2 or more amino acids linked in a chain by peptide bonds. Peptides are distinguished from protein on the basis of size, and as an arbitrary benchmark can be understood to contain approximately 50 or fewer amino acids. As used herein, the EGYR molecule to be tested according to the methods of the invention is referred to as a peptide. The terms peptide and polypeptide may be used interchangeably.

LARP1 fragment peptides including the EGYR peptide can be produced by treatment with one or more endoproteases such as trypsin and its variants. In one embodiment, the sample is digested with trypsin or a trypsin variant.

In particular embodiments, the proteins in the sample are reduced and alkylated by the addition of an alkylating agent such as iodoacetamide or chloroacetamide, before digestion.

The purpose of alkylation is to prevent the di-sulfides from re-forming. The fragmented (e.g. sheared, digested or cleaved) sample may be subjected directly to mass spectrometric analysis or may be processed prior to MS analysis.

In some embodiments, the processing steps include one or more purification steps. In some embodiments, the processing steps include solid-phase extraction, and/or applying the sample to an anion or cation exchange column under conditions suitable to retain LARP1-derived EGYR peptide on the column; eluting LARP1-derived EGYR peptide from the column; and collecting the eluted LARP1-derived EGYR peptide for further processing or ionization. In some embodiments, the processing steps comprises chromatography.

Chromatography

Prior to detection, such as via mass spectrometry, it can be advantageous to fractionate the cleaved/(e.g. digested) sample, such as by using chromatography. Methods of fractionation of a protein sample are well known in the art, and include without limitation paper chromatography, thin layer chromatography (TLC), liquid chromatography, column chromatography, fast protein liquid chromatography (FPLC), ion exchange chromatography, size exclusion chromatography, affinity chromatography, high performance liquid chromatography (HPLC), poly acrylamide gel electrophoresis (PAGE), capillary electrophoresis (CE) and reverse phase high performance liquid chromatography (RP-HPLC) amongst others.

Thus, according to another embodiment, the cleaved sample (protein digest) is optionally subjected to chromatographic separation prior to detecting for a LARP1 fragment peptide with the amino acid sequence: EGYR, using mass spectrometry.

Chromatography is a well-understood field and the person skilled in the art would understand how to, and be able to, use any of these techniques to separate the proteins and peptides in a sample according to the methods of the invention, such as described in "Mass Spectrometry: A textbook by Jurgen Gross, or "Mass Spectrometry principles and applications" by Edmond de Hoffmann and Vincent Stroobant.

In particular embodiments, the sample, such as the digested/cleaved sample, is subjected to chromatographic separation comprising liquid chromatography (LC).

In particular embodiments, the LC is selected from: normal phase liquid chromatography (NPLC), reverse phase liquid chromatography (RPLC), high performance liquid chromatography (HPLC) and ultra high performance liquid chromatography (UHPLC). For peptide digests reverse phase liquid chromatography (RPLC), high performance liquid chromatography (HPLC) and ultra high performance liquid chromatography (UHPLC) are particularly suitable.

In a particular embodiment, the liquid chromatography comprises reverse phase chromatography.

In a particular embodiment, the liquid chromatography comprises high performance liquid chromatography (HPLC) or ultra-performance liquid chromatography (UPLC).

Mass Spectrometry

The methods of the invention rely on the detection of the EGYR peptide in a biological sample. The ability to detect the presence of, and optionally the amount of EGYR peptide in a sample is most efficiently carried out using mass spectrometry.

Mass spectrometry techniques are well-understood and the person skilled in the art would understand how to, and be able to, use any of these techniques to separate the proteins and peptides in a sample according to the methods of the invention.

Typically, mass spectrometry is performed using a mass spectrometer, which includes an ion source capable of generating gas phase ions from a sample (such as a sample containing LARP1 fragment peptides and/or peptide standards). The gas phase ions are then separated according to their mass-to-charge ratio (m/z) and detected. Suitable techniques for producing gas phase ions for use in the disclosed methods include without limitation electrospray ionization (ESI), matrix-assisted laser desorption-ionization (MALDI), surface-enhanced laser desorption-ionization (SELDI) and chemical ionization.

Separation of ions according to their m/z ratio can be accomplished with any type of mass analyser, including quadrupole mass analysers (Q), time-of-flight (TOF) mass analysers (for example linear or reflecting) analysers, magnetic sector mass analysers, 3D and linear ion traps (IT), Fourier-transform ion cyclotron resonance (FT-ICR) analysers, and combinations thereof (for example, a quadrupoletime-of-flight analyser, or Q-TOF analyser). In some embodiments, the mass spectrometric technique is tandem mass spectrometry (MS/MS) and the presence of a LARP1 fragment peptide is detected. Typically, in tandem mass spectrometry a LARP1 fragment peptide entering the tandem mass spectrometer is selected and subjected to collision induced dissociation (CID). The spectra of the resulting fragment ion is recorded in the second stage of the mass spectrometry, as a so-called CID spectrum. Because the CID process usually causes fragmentation at peptide bonds and different amino acids for the most part yield peaks of different masses, a CID spectrum alone often provides enough information to determine the presence of a peptide such as a LARP1 fragment peptide. Suitable mass spectrometer systems for MS/MS include an ion fragmentor and one, two, or more mass spectrometers, such as those described above. Examples of suitable ion fragmentors include, but are not limited to, collision cells (in which ions are fragmented by causing them to collide with neutral gas molecules), photo dissociation cells (in which ions are fragmented by irradiating them with a beam of photons), and surface dissociation fragmentor (in which ions are fragmented by colliding them with a solid or a liquid surface). Suitable mass spectrometer systems can also include ion reflectors.

For example ionization of the sample may be performed by electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc. A LARP1-derived peptide, such as EGYR, may be ionized in positive or negative mode. In some embodiments, LARP1-derived EGYR peptide are ionized by ESI (such as by heated ESI) in positive mode.

In mass spectrometry techniques generally, after the sample has been ionized, the positively or negatively charged ions thereby created may be analysed to determine a mass-to-charge ratio. Suitable analysers for determining mass-to-charge ratios include Orbitrap analysers, quadrupole analysers, ion trap analysers, and time-of-flight (TOF) analysers. Exemplary ion trap methods are described in Bartolucci, et at, Rapid Commun. Mass Spectrom. 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM).

Preferably, the mass-to-charge ratio is determined using a quadrupole analyser. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the specificity of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analysed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

Thus, in a particular embodiment, the detecting, i.e. the detecting for the presence of EGYR fragment peptide in the sample, e.g. in the protein digest, is done using methods that involve mass spectrometry (MS) or comprises MS. Thus, in a particular embodiment, a putative EGYR peptide containing sample or fraction isolated by chromatography is subjected to mass spectrometry to determine whether or not the EGYR peptide is present.

In any of the methods provided herein which require ionization of EGYR peptide, mass spectrometry is preferably performed in positive ion mode. Alternatively, mass spectrometry is performed in negative ion mode.

Various ionization sources, including for example atmospheric pressure chemical ionization (APCI), electrospray ionization (ESI), and heated ESI, may be used in embodiments of the present invention. In certain preferred embodiments, EGYR peptide is ionized using heated ESI in positive ion mode.

In some embodiments, the LARP1-derived EGYR fragment peptide is detected by the detection of fragment ions of the EGYR fragment peptide, for example using tandem mass spectrometry.

In another embodiment, the detecting comprises tandem mass spectrometry (MS:MS).

Using tandem MS, the inventors have been able to fragment EGYR peptide and detect it with a diagnostic m/z fragment peak of about 136.1. Thus, in a particular embodiment, a putative EGYR peptide containing sample or fraction isolated by chromatography is fragmented in MS:MS mode and the presence of a moiety with an m/z of about 136.1 is searched for, and if present this is selected and quantified. In a particular embodiment, the presence of EGYR peptide in a sample is verified if following tandem MS there is identified a molecule with an m/z of about 136.1.

Embodiments utilizing tandem mass spectrometry comprise fragmenting the charged EGYR peptide ions into EGYR peptide fragment ions. In one embodiment the EGYR peptide fragment ions have an m/z of about 136.1.

In any of the methods provided herein which utilize tandem mass spectrometry, tandem mass spectrometry may be conducted by any method known in the art, including for example, multiple reaction monitoring, precursor ion scanning, or product ion scanning.

The methods of the invention include subjecting the sample to proteolytic fragmentation (e.g. degradation or cleavage) followed by ionization under conditions suitable to produce charged EGYR-derived peptide ions detectable by mass spectrometry; determining by mass spectrometry the amount of one or more ions from the one or more EGYR-derived peptides; and using the amount of the determined ions to determine the presence of and/or amount of LARP1 protein in the sample. Optionally, the sample of fragmented proteins is subjected to chromatography to separate out the various cleaved peptides and the fraction that comprises peptides with the EGYR amino acid sequence is then subjected to the mass spectrometry.

In some embodiments, ions are determined from EGYR peptide. In one embodiment charged EGYR fragment ion to be detected has an m/z of about 136.1.

One or more steps of the methods of the invention may be performed using automated machines. In certain embodiments, one or more purification steps are performed on-line, and suitably all of the purification and mass spectrometry steps may be performed in an on-line fashion.

Quantitation by MS

In addition to detecting for the presence of EGYR peptide in a sample of interest it is also possible, and useful, to quantify the amount in the sample.

According to a second aspect of the invention there is provided a method for determining the amount of LARP-1 protein in a sample, comprising:
 (1) subjecting the sample to ionisation under conditions suitable to produce charged EGYR peptide ions detectable by mass spectrometry;
 (2) determining by mass spectrometry the amount of charged ions produced in (a); and
 (3) using the determined amount of ions in step (b) to determine the amount of LARP-1 protein in the sample.

To quantitate the amount of LARP1 in th sample a standard curve of known "spiked" amounts of recombinantly produced LARP1 in a control solution treated the same way as the test sample is treated and then correlating ion intensity of a isotopically labelled peptide with non-labelled peptides resulting from recombinant LARP1.

Specific embodiments for the second and subsequent aspects of the invention are as for the first aspect mutatis mutandis.

In a particular embodiment, the positively charged parental EGYR ion has a monoisotopic mass of 523.24 and an m/z of 262.63.

In a particular embodiment, the charged EGYR fragment ion to be detected has an m/z of about 136.1.

In a particular embodiment, the methods of the various aspects of the invention comprise quantifying the EGYR fragment peptide in a sample. Suitably, the quantification is done by reference to normal values or by comparison to one or more reference standard.

Exemplary reference standards include blank plasma or serum spiked with an EGYR peptide or an isotopically labelled variant thereof, such as isotopically labelled EGYR peptide.

Suitably, quantifying the amount of EGYR fragment peptide comprises comparing the amount of detected peptide to an EGYR peptide standard of known amount. The EGYR peptide standard may be labelled, such as fluorescently labelled or isotopically labelled. In one embodiment, the EGYR peptide standard is isotopically labelled.

Methods of labelling peptides with heavy isotopes are well known in the art

"Isotopically-labelled" refers to a molecule that includes one or more stable heavy isotopes in a greater-than-natural abundance. Examples of suitable labels include deuterium ($^{2}H$), $^{13}C$, $^{15}N$, $^{35}S$, $^{17}O$ and $^{18}O$. One or more isotopic labels can be incorporated at one or more positions in the molecule and one or more kinds of isotopic labels can be used on the same isotopically labelled molecule.

If the EGYR standard is labelled it can be spiked into the test sample. By spiked we mean added to the sample in a known amount so that the amount of EGYR in the test sample can be determined based on the intensity of the standard. When spiking the sample with EGYR standard it is important that the spiked peptide can be distinguished from the EGYR peptide in the sample.

In one embodiment, such methods include comparing an amount of the EGYR fragment peptide to an EGYR peptide standard of known amount.

This is most suitably done by generating a standard curve using known amounts of recombinant LARP1, e.g. isotopically labelled. This way you will know how much of your isotopically labelled peptide corresponds to how much actual LARP1 protein in your sample.

By way of example, the change in relative peak intensity before and after the addition of a peptide standard can be used to calculate the amount of EGYR peptide present in a biological sample, thus providing quantification of LARP1 in the sample. When a non-isotopically labelled peptide standard is used, a mass spectrum of the protein digest is obtained both with and without addition of the non-isotopically labelled peptide standard. The ratio of the intensity of the signals with and without the addition of the non-isotopically labelled peptide standard reflects the relative amounts (or concentrations) of the EGYR LARP1-derived fragment peptide present in a biological sample, and thus the amount of LARP1 present in the sample.

When an isotopically labelled peptide standard is used, typically the combined sample (peptide standard plus protein digest) is analysed by mass spectrometry, and the ratios of the mass spectral signal intensities for the labelled peptide standard and the sample peptides are measured. A mass spectrum of a sample containing both sample peptides and the added peptide standard typically includes one or more pairs of separated signals that are due to a sample peptide and its corresponding peptide standard. The ratio of the intensity of the signals in each pair reflects the relative amounts (or concentrations) of each peptide present in the sample. Since the amount (or concentration) of the peptide standard is known, the amount (or concentration) of the sample peptide can be calculated by multiplying the ratio of the intensity of the signal for the sample peptide to the intensity of the signal for the peptide standard by the known amount (or concentration) of the peptide standard. Furthermore, since the sample peptides are present in amounts (or concentrations) that are the same as (or related by a known ratio to) the amounts (or concentrations) of the proteins originally in the sample, a determination of the amounts (or concentrations) of the sample peptides also permits a determination of the amounts (or concentrations) of the proteins in the sample. Since the concentrations of the peptide standards are known, the concentration of the sample peptides (and the proteins they are derived from, such as full length LARP1) can be calculated using the ratios.

EGYR Peptide Standard

Peptide standards for use in quantitating LARP1-derived EGYR peptide in a biological sample are also disclosed.

Such peptide standards consist of or comprise a peptide with the amino acids EGYR and are optionally isotopically labelled. In one embodiment, the EGYR peptide standard is isotopically labelled with $^{15}$N and/or $^{13}$C. Suitably, it is the last amino acid (arginine) which is labelled. Arginine is an easy choice and widely used in for example SILAC (Stable isotope with Amino Acids in Cell Culture) labelling. Useful isotopically labelled peptide standards have a predictable number of sites where the heavy isotope replaces a non-heavy isotope yielding a peptide with a predictable mass difference from a peptide that does not have any heavy isotopes incorporated. Thus, the isotopic-labelling of the peptide standards yields separate distinct mass spectrometric signals from peptides obtained from the biological samples. These isotopically labelled peptide standards can be used to quantify proteins present in biological samples.

A standard is a substance or solution of a substance of known amount, purity or concentration. A standard can be compared (such as by spectrometric, chromatographic, or spectrophotometric analysis) to an unknown sample (of the same or similar substance) to determine the presence of the substance in the sample and/or determine the amount, purity or concentration of the unknown sample. In one embodiment a standard is a peptide standard. An internal standard is a compound that is added in a known amount to a sample prior to sample preparation and/or analysis and serves as a reference for calculating the concentrations of the components of the sample. Isotopically-labelled peptides are particularly useful as internal standards for peptide analysis since the chemical properties of the labelled peptide standards are almost identical to their non-labelled counterparts. Thus, during chemical sample preparation steps (such as chromatography, for example, HPLC) any loss of the non-labelled peptides is reflected in a similar loss of the labelled peptides.

Isotopically-labelled peptide standards of known concentration and molecular weight can be synthesized from isotopically labelled amino acids. Peptide synthesis is well known in the art (see for example, Atherton and Sheppard, Solid Phase Peptide Synthesis: a Practical Approach published by published by Oxford University Press, USA, and Chan and White Fmoc Solid Phase Peptide Synthesis: A Practical Approach, published by Oxford University Press, USA).

Thus, according to an ninth aspect of the invention there is provided an isolated peptide comprising the amino acid sequence EGYR. Such a peptide may be referred to as a peptide standard. Such peptide standard may be synthesised. Methods for synthesising peptides are well known. In one embodiment the peptide consists of the amino acid sequence EGYR. In particular embodiments, the peptide is labelled. Suitably the peptide is fluorescently labelled or is isotopically labelled. In particular embodiments, the EGYR peptide is labelled with an isotope selected from: deuterium ($^{2}$H), $^{13}$C, $^{15}$N, $^{35}$S, $^{17}$O and $^{18}$O. In particular embodiments, the EGYR peptide is labelled with an isotope selected from: $^{13}$C and/or $^{15}$N.

Suitably, you want the peptide to be 4 to 10 Daltons heavier, which would require 4 to 10 Carbons+Nitrogens to be labelled. It does not matter which atoms are labelled as long as it is consistent between all conditions. In particular embodiments, the arginine amino acid contains four $^{15}$N and six $^{13}$C, leading to a mass shift of +10 Da.

A distinction between the m/z of the EGYR peptide in the sample and that of the labelled internal standard facilitates quantitation.

Suitably, the monoisotopic mass of the labelled EGYR is 534.2 as compared to the monoisotopic mass of 524.2 of the unlabelled EGYR.

As can be seen from the Examples, the mass of the isotopically labelled EGYR standard is 534.2 as compared to the mass 524.2 of the unlabelled EGYR in the sample.

Thus, in a particular embodiment, the EGYR standard has an mass that differs from the mass of the EGYR in the sample by at least 5, such as 8, 10, 12, or 15 atomic mass units (amu).

In a particular embodiment, the EGYR standard has a mass of about 534.2.

In particular embodiments of the methods presented herein which determine the amount of EGYR peptide (or LARP1 protein) in a sample, a separately detectable internal standard is provided in the sample, the amount of which is also determined in the sample. In these embodiments, all or a portion of both the EGYR peptide and the internal standard present in the sample is ionized to produce a plurality of ions detectable in a mass spectrometer, and one or more ions produced from each are detected by mass spectrometry. In these embodiments, the presence or amount of ions generated from the EGYR peptide of interest may be related to the presence of amount of LARP1 protein in the sample.

The present invention also contemplates kits for a LARP1-derived EGYR peptide quantitation assay. The kit may include packaging material and measured amounts of isolated EGYR peptide or an isotopically labelled internal standard, such as a labelled EGYR peptide, in amounts sufficient for at least one assay. Typically, the kits will also include instructions for using the packaged reagents in a quantitation method to detect the presence of EGYR peptide in a test sample. The instructions may detail one or other of the methods of the invention as detailed herein, such as those according to any of the first to seventh aspects.

Applications

The ability to detect the presence of elevated levels of LARP1 in a sample by detection of just the EGYR peptide from LARP1 protein is surprising. Not only because EGYR is such a small peptide, or because detection of other LARP1 peptides has been found to be less accurate (statistically) but because it might have been assumed that other proteins in blood, such as Complement C5 beta chain, would be capable of releasing EGYR peptide following trypsin digestion.

The present invention has various applications, including: i) prognosing the development of cancer; (ii) predicting the responsiveness to a therapeutic treatment; (iii) method of identifying subjects that are in early stages of cancer development; (iv) detecting the presence of pre-invasive cancer; (v) detecting the presence of or development of STIC; (vi) determining the stage of a cancer; and (vii) diagnosing cancer.

In one embodiment the methods of the invention can be used to for prognosing the development of cancer.

According to a third aspect of the invention there is provided a method for prognosing the development of cancer, comprising
(a) treating a biological sample from a patient with one or more agents capable of cleaving the proteins in the sample;
(b) subjecting the treated sample mass spectrometry;
(c) determining by mass spectrometry the amount of ionised EGYR peptide; and
(d) using said amount determined in (c) to determine the amount of EGYR peptide in the treated sample, wherein elevated levels of EGYR peptide in the treated sample relative to normal or control levels indicates a poorer prognosis with respect to the development of cancer.

Suitably in step (a) the proteins in the biological sample are contacted with trypsin or a trypsin variant capable of cleaving the proteins after arginine and lysine residues.

Suitably in step (b) the sample is treated to ionisation under conditions suitable to produce one or more charged ions detectable by mass spectrometry.

The cancer can be any type of cancer, including ovarian cancer, breast cancer, pancreatic cancer, colon cancer and hepatocellular cancer.

In particular embodiments, the cancer is selected from the group consisting of: ovarian cancer, breast cancer, pancreatic cancer, colon cancer and hepatocellular cancer. The cancer may be refractory cancer or a metastatic cancer.

The methods of the present invention involve comparing the level of LARP1 protein in a sample (e.g. serum or plasma sample) from a subject with normal levels (e.g. reference values) or the level of LARP1 protein in a control sample. The control sample is typically a matched sample (e.g. a serum or plasma sample) taken from a subject who is known not to be suffering from cancer, for example a healthy control subject. Alternatively, the control sample can be a sample taken from a subject with a benign tumour, for example a benign ovarian tumour. In some embodiments, the control sample has no LARP1 protein, or LARP1 protein is undetectable in the control sample.

An elevated level of LARP1 protein (or EGYR peptide as surrogate of LARP1) in the sample from the subject compared to the level in the reference value or control sample is indicative of poor prognosis of said cancer. In other words, the subject has a poor or low chance of survival, for example over a particular period of time. In other words, the subject is unlikely to survive for a particular period of time after the diagnosis of cancer is made. Without wishing to be limited by specific values, "poor prognosis" or "poor chance of survival" can mean, for example, that the subject has a 60% or lower, for example 50%, 40%, 30%, 20% or 10% chance of surviving for 100, 200, 400, 600, 800 or 1000 days after the date of diagnosis.

By "an elevated level of LARP1 protein" is meant a significantly higher level, in particular a statistically significantly higher level. Statistical tests known in the art can be used, for example the Wilcoxon signed rank sum test, the Mann-Whitney test or Cox Regression analyses. Statistical significance can be determined based on any suitable p-value, for example p<0.05, p<0.01 or pO.001.

Without wishing to be limited by specific values, an example of a typical elevated level of LARP1 protein in a sample is in the region of 750 to 1250 pg/ml, for example from 800 to 1200 pg/ml, from 900 to 1150 pg/ml, from 950 to 1100 pg/ml or around 1000 pg/ml. An example of a typical level of LARP1 protein in a control sample is in the region of 0 to 200 pg/ml, for example from 50 to 150 pg/ml or around 100 pg/ml.

In one embodiment, the disclosed methods can be used to determine the progression of the cancer, for example by correlating the detected amount of the EGYR fragment peptide to progression of the cancer.

The disclosed methods are particularly suited for monitoring disease progression in a subject. Such methods involve detecting an amount of LARP1 in a biological sample from a subject at a first time point, detecting an amount of LARP1 in a biological sample from a subject at a second time point, and comparing the amount of LARP1 at the two time points. It has been found that the expression level of LARP1 in a tumour correlates with the severity of the cancer. Thus, a decrease in the amount of LARP1 present in a biological sample, for example as measured by the presence of EGYR LARP1 fragment peptide, would correlate with regression of the cancer. Conversely, an increase in the amount of EGYR LARP1 fragment peptide (indicating an increase in LARP1) could correlate to a progression of the cancer, for example progression to a metastatic form of cancer.

The present inventors hypothesize that plasma LARP1 is indicative of response to treatment with certain drugs. In particular, an elevated level of LARP1 indicates that the subject will be more responsive to a drug designed to inhibit LARP1, cMYC or a component of a stress response pathway but will be less responsive to chemotherapy, radiotherapy or certain targeted therapies (such as mTOR inhibitors, PARP inhibitors).

Thus, LARP1-derived EGYR peptide may also be quantitated in patient samples from a subject being treated for cancer in order to gauge the efficacy of a treatment. A decrease in the amount of LARP1-derived EGYR peptide in the patient's sample following a therapeutic treatment indicating that the treatment is or was effective.

In one embodiment, the disclosed methods can be used to monitor the efficacy of a treatment by determining the change in the amount of LARP1 protein in the biological sample at different stages of the treatment (e.g. before, during and/or after), suitably the biological sample is a blood sample or blood-derived sample such as plasma or serum.

Accordingly, in a fourth aspect of the invention there is provided a method of determining whether a cancer patient responds to a therapeutic treatment, comprising detecting the level of LARP1 protein in a biological sample from the patient after the therapeutic treatment; and comparing the level of LARP1 protein in said sample with the level of LARP1 protein in a control sample, wherein the detecting comprises mass spectrometry and wherein an elevated level of LARP1 protein in said sample from said subject compared to the level of LARP1 protein in said control sample indicates that the subject does not respond to said therapeutic treatment. Conversely, if an elevated level of LARP1 protein is not found in said serum or plasma sample, this indicates that the subject does respond to the therapeutic treatment or is responding to the therapeutic treatment.

By therapeutic treatment we mean a treatment designed to treat the cancer in the patient. By way of examples, such therapeutic treatment could be chemotherapy or radiotherapy or could be administration of an anticancer agent/drug.

In one embodiment, the biological sample is a serum or plasma sample. In one embodiment, the control sample is a pre-treatment sample from the patient. In one embodiment, the therapeutic treatment is radiotherapy or chemotherapy. In one embodiment, the therapeutic treatment is administration of an anti-cancer drug.

The anti-cancer drug can be, for example, a chemotherapeutic drug such as bleomycin, carboplatin, cisplatin, cyclophosphamide, dacarbazine, docetaxel, doxorubicin, etoposide, 5-fluorouracil, folinic acid, gemcitabine, irinotecan, oxaliplatin, paclitaxel, or a combination chemotherapeutic regimen such as AC (doxorubicin and cyclophosphamide), BEP (bleomycin, etoposide and platinum agent), Carbo/taxol (carboplatin and paclitaxel), FOLFIRINOX (5-flurouracil, folinic acid, irinotecan, oxaliplatin) or a chemotherapy agent or combination of agents given with a targeted therapy such as bevacizumab, or stem cell targeted therapy.

Detecting Pre-Invasive Cancer

The inventors also hypothesise that LARP1 levels can be used to predict development of a multitude of cancers, including ovarian, breast and pancreatic cancer. Pancreatic cancer is believed to have a slow development has, perhaps as long as 10 or 12 years, but at the time of diagnosis (typically when it metastasises) it has a rapid disease progression often leading to death within 6 months. The ability to pick up the development of pancreatic cancer during this earlier development phase is therefore important. The inventors believe that LARP1 protein levels in the blood could signal early cancer development, including pancreatic cancer.

As part of normal cancer screening subjects could be tested for blood LARP1 levels in accordance with the methods of the present invention and if higher than normal levels are detected the subject could undergo further diagnostic assessments to identify which cancer they may be developing.

According to a fifth aspect of the invention there is provided a method of identifying subjects that are in early stages of cancer development comprising detecting the level of LARP1 protein in a serum or plasma sample from the subject; and comparing the level of LARP1 protein in said sample with the level of LARP1 protein with a reference value or in a control sample, wherein an elevated level of LARP1 protein in said sample from said subject compared to the level of LARP1 protein in said reference value of in the control sample indicates that the subject is in early stages of cancer development.

In particular embodiments the cancer is one selected from the group consisting of: ovarian cancer, breast cancer, pancreatic cancer, colon or colorectal cancer, hepatocellular cancer, cervical cancer, lung cancer and prostate cancer.

Following this simple LARP1 blood test, a subject that is identified as one that is in early stages of cancer development can be selected for further diagnostic tests to identify the particular cancer that they possess or are developing.

In this aspect, the detection could be carried out using any techniques, including immunoassays (e.g. enzyme-linked immunosorbent assay; ELISA) capable of determine the amount of LARP1 protein or any LARP1-derived peptide in the blood. Such methods are taught, for example in WO2016/075455. However, in a preferred embodiment the detection comprises mass spectrometry in line with the methods of the invention described herein.

Detecting STIC

The inventors have identified that the level of LARP1 protein in circulating blood correlates with advancement of ovarian cancer. In particular, the level of LARP1 in the blood (including in serum or plasma) can be used to predict the development of cancer, such as ovarian cancer, and in particular can predict the presence or development of STIC.

Normal ovarian cells can develop serous tubal intraepithelial lesions (STIL) which are pre-cancerous lesions that can be recognised by p53 signature but exhibit no significant morphological change. Over time these can develop into serous tubal intraepithelial carcinoma (STIC), a pre-malignant stage where malignant cells start to replace normal tubular epithelium. Current ovarian cancer detection blood tests, that measure CA125 levels, cannot pick up STIL or STIC. There is a need in the art to pick up cancers when at the STIC stage (pre-invasive ovarian cancer stage) to allow earlier therapeutic intervention.

The inventors have detected that LARP1 is strongly present in STIC lesions and have been able to detect elevated LARP1 levels in blood of these patients. Whilst an increase in LARP1 can be detected in serum and whole blood, the inventors have found that plasma samples yield more sensitive measurements. This may be because plasma doesn't contain clotting factors and other proteins that could cross-react.

As can be seen in Example 4, BRCA patients that had plasma LARP1 levels of about 25 µg/ml or higher were more likely to have STIC or other relevant pre-invasive lesion. The methods of the invention can therefore be applied to the identification of patients with STIC.

The inventors have also discovered that serum LARP1 is present in patients with invasive ovarian cancer and the level correlates with diagnosis (see Example 3). The methods of the invention can therefore be applied to the diagnosis of ovarian cancer.

Serum LARP1 also correlates with survival in patients with advanced ovarian cancer (see Example 3). The methods of the invention can therefore be applied to the prognosis of patients with advanced ovarian cancer.

The inventors have also discovered that serum LARP1 level correlates with the stage of cancer (see Example 3). The methods of the invention can therefore be applied to the staging of a patient with ovarian cancer.

The methods of the invention can therefore be utilised to diagnose, prognose and/or stage a patient with ovarian cancer.

The ability to detect STIC in a subject is particularly useful.

According to a sixth aspect of the invention there is provided a method of predicting the presence of serous tubal intraepithelial carcinoma (STIC) in a subject comprising detecting the level of LARP1 protein in a serum or plasma sample from the subject; and comparing the level of LARP1 protein in said sample with a reference value of LARP1 protein or with the level of LARP1 in a control sample, wherein an elevated level of LARP1 protein in said sample from said subject compared to the reference value or the level of LARP1 protein in the control sample predicts that the subject has STIC.

In one embodiment the subject is one that has an increased risk of developing ovarian cancer, such as possessing germline driver mutations in genes such as BRCA1 and/or BRCA2.

It is likely that an increase in LARP1 protein in the circulating blood of such a person signifies development of ovarian cancer or pre-ovarian cancer (STIC). It is therefore envisaged that LARP1 protein levels in the blood can be used as a biomarker for the presence of a STIC lesion who are likely to subsequently develop ovarian cancer and so can be included in the repertoire of screening for this disease. Identifying the subject before development of ovarian cancer may allow steps to be taken to remove the STIC (such as with surgery) or other, future, non-surgical approaches.

The reference value or threshold value will be an indicative normal value. Such reference value can be established following assessments of values from normal patients (i.e. those without STIC) according to standard clinical and statistical practice.

As a guide, a threshold level of LARP1 in the plasma of a subject that signifies likelihood of having STIC may be selected from the group consisting of: 15, 18, 20, 22, 25, 26, 27, 28, 29, 30, 31, 32 and 35 µg/ml. The threshold value selected based on the data in the present Examples (35 patients) is 25 µg/ml. It will be appreciated that the clinically accepted threshold level may differ from this value and will be based on data from many hundreds to thousands of patients. It will also be appreciated that the threshold level will alter depending on the sample source. Thus, the threshold level for whole blood, plasma and serum may be slightly different.

By "threshold level or value" we mean a value which has been selected by the health authority as signifying a positive result when crossed (higher than) or a negative result if not crossed (less than). Such a threshold value may differ between patient sub-groups. For example, based on age, genetic make-up (e.g. presence of driver mutations in key genes), ethnicity etc.

In this aspect, the detection could be carried out using any techniques, including immunoassays (e.g. enzyme-linked immunosorbent assay; ELISA) capable of determine the amount of LARP1 protein or any LARP1-derived peptide in the blood. Suitable methods are disclosed in WO2016/075455. However, in a preferred embodiment the detection comprises mass spectrometry in line with the methods of the invention described herein.

In a particular embodiment of any of the aspects disclosed herein involving a cancer patient, the patient comprises cancer-predisposing mutations in its genomic DNA. In particular embodiments, the patient possesses germline BRCA1 or BRCA-2 mutations.

In particular embodiments, the patient comprises germline driving mutations in a gene selected from: BRCA1, BRCA2, KRAS, P53, ALK and HER2. In another embodiment, the patient has a hereditary cancer-predisposition syndrome selected from BRCA, Lynch and Li Fraumeni identified by genetic analysis, family or personal history alone (Rahmen N. Nature, 2014).

According to the seventh aspect, the invention provides methods for diagnosing or predicting risk of developing cancer. These methods include providing or acquiring a biological sample obtained from a patient; subjecting the biological sample to one or more processing steps to cleave the proteins in the sample to smaller peptides, wherein if LARP1 protein is in the sample the peptides produced include EGYR peptide; subjecting the processed sample to ionization under conditions suitable to produce one or more multiply charged ions detectable by mass spectrometry; determining by mass spectrometry the amount of one or more ions from the LARP1-derived EGYR peptide; and using the determined ion amounts to determine the amount of LARP1 protein in the biological sample or EGYR peptide in the processed sample. In these methods, elevated LARP1 protein levels in the biological sample relative to normal indicate the presence of or risk of developing cancer.

According to an eighth aspect of the invention there is a method for determining the amount of LARP-1 protein in a biological sample, comprising:
 (d) treating the biological sample with trypsin/trypsin variant to cleave the proteins in the sample;
 (e) subjecting the treated sample to ionisation under conditions suitable to produce charged EGYR peptide ions detectable by mass spectrometry;
 (f) detecting the charged ions produced in (b); and
 (e) using the amount of ions in step (c) to determine the amount of LARP-1 protein in the sample.

Suitably, the sample subjected to mass spectrometry is spiked with an internal standard so that the amount of EGYR-derived protein, e.g. LARP1 can be quantitated.

Specific embodiments for the third, fourth, fifth, sixth, seventh and eighth aspects of the invention are as for the first aspect mutatis mutandis.

LARP1-derived EGYR peptide may be quantitated in patient samples from a subject in order to detect the presence of pre-invasive cancers. In detecting the presence of pre-invasive cancers, levels of LARP1-derived EGYR peptide from the patient sample are compared to normal levels in samples or to reference values. Elevated levels of LARP1-derived EGYR peptide in a patient sample relative to normal levels or reference values indicates the presence of pre-invasive cancer in the patient.

LARP1-derived EGYR peptide may be quantitated in patient samples from a subject in order to detect the presence of or development of STIC. In detecting the presence of or development of STIC, levels of LARP1-derived EGYR peptide from the patient sample are compared to normal levels in samples. Elevated levels of LARP1-derived EGYR peptide in a patient sample relative to normal levels indicates the presence of or risk of developing STIC in the patient. An increase in the amount of LARP1 protein in the patient's circulating blood, serum or plasma indicates development of STIC. As such, the methods of the invention can be applied to detecting the presence of or monitoring progression of STIC in a patient.

LARP1-derived EGYR peptide may also be quantitated in patient samples from a subject in order to determine the stage of cancer. This is particularly suitable if the biological sample is plasma.

The following Examples serve to illustrate the invention. These Examples are in no way intended to limit the scope of the invention, but rather as examples from which equivalents will be recognized by those of ordinary skill in the art.

Unless it is apparent from the context, each of the embodiments listed above can be applied for use in any of the aspects of the invention.

EXAMPLES

Example 1: LARP1 from the Plasma of Patients with Advanced Cancer

Plasma samples were obtained from 67 patients with advanced cancers. Cancer types included pancreatic (9), colorectal (7), renal (1), gastric (1), gastro-esophageal (1), lung (7), mesothelioma (3), esophagus (2), osteosarcoma (1), ovarian (13), ACUP (3), adrenal (1), anal (1), breast (4), cholangiocarcinoma (7), thymus (1), uterine (3). For comparison, 10 non age-matched controls were used. For each sample, 100 µl of plasma was extracted with 300 µl of acetone. Extracted pellets were re-suspended in 95 µl 100 mM Tetraethylammonium bromide (TEAB), 5 µl of 2% Sodium dodecyl sulfate (SDS) and 5.3 µl 20 mM Tris(2-carboxyethyl)phosphine hydrochloride (TCEP) and incubated for 1 hr at 55° C. Then, 5.5 µl of 150 mM Iodoacetamide (IAA) and incubated for further 1 hr in the dark. 10 µl of trypsin solution was added and incubated overnight at 37° C. with agitation. Custom-made isotopically labelled Internal standard (IS) peptides (UC13/N15 of arginine or lysine residues) were added to the trypsinized plasma samples at a concentration of 1 µg/ml. For desalting, samples supernatant were loaded in Oasis HLB cartridges, pre-conditioned with 1 mL 100% acetonitrile (ACN) and equilibrated with 1 mL 99% $H_2O$/1% ACN/0.1% TFA. Samples were washed with 1 mL 99% $H_2O$/1% ACN/0.1% TFA and eluted with 0.5 mL 50% $H_2O$/50% ACN. 1 mg/ml stock solutions of reference peptide were prepared and aliquots frozen at −80° C. until use. Fresh calibration standards were prepared by diluting the stock solution in water to the following concentrations: 0, 1, 3, 10, 30, 100, 300 and 1000 ng/ml. All plasma samples were run between two calibration curves.

Peptides were resolved using an ultra-performance liquid chromatography system (Accela UPLC, Thermo Scientific, UK) equipped with an ACE UPLC C18-Amide, 1.7 µm, 100×2.1 mm column (Anachem, UK) and a mobile phase consisting of a mixture of ACN (0.1% formic acid)/$H_2O$ (0.1% formic acid) at a flow rate of 200 µl/minute. Eluting compounds of interest were detected using a triple stage quadrupole Vantage mass spectrometry system (Thermo Scientific, UK) equipped with an electrospray ion source. Samples will be analyzed in the Multiple Reaction Monitoring (MRM), positive ion modes at a spray voltage of 3000 V. Nitrogen was used as sheath and auxiliary gas at a flow rate of 50 and 20 arbitrary units, respectively. Argon was used as collision gas with pressure of 1.5 mTorr. The optimum multiple reaction monitoring transitions and collision energy (CE) for eluting peptides were as follows: Sequence 1: EGYR (524.2→137.1, CE 37V), EGYR IS (534.2→137.1, CE 37V), Sequence 2: LDIFK (635.4→86.1, CE 35V), LDIFK IS (643.3→86.1, CE 36V), Sequence 3: DHFNK (330.6→84.1, CE 34V), DHFNK IS (668.3→253.0, CE 36V), Sequence 4: FWAFLK (406.2→120.0, CE 35V), FWAFLK IS (410.2→120.0, CE 35V), Sequence 5: NLDIDPK (407.7→244.1, CE 16V), NLDIDPK IS (822.5→251.9, CE 36V), Sequence 6: RLEDFR (418.3→322.1, CE 17V), RLEDFR IS (423.2→332.1, CE 16V), Sequence 7: LQEYLGK (425.8→86.1, CE 22V) and LQEYLGK IS (429.7→86.1, CE 21V).

Peptides:

| 1 | EGYR | SEQ ID NO: 3 |
| 2 | LDIFK | SEQ ID NO: 4 |
| 3 | DHFNK | SEQ ID NO: 5 |
| 4 | FWAFLK | SEQ ID NO: 6 |
| 5 | NLDIDPK | SEQ ID NO: 7 |
| 6 | RLEDFR | SEQ ID NO: 8 |
| 7 | LQEYLGK | SEQ ID NO: 9 |

Data was pooled to obtain a collective "LARP1 score". Healthy controls had a mean LARP1 score of 0.17 ng/ml with range 0.07-0.33 ng/ml. In patients with advanced cancers, there was a mean LARP1 score of 0.81 ng/ml with range 0.08-13.38 ng/ml. Of these samples, the sequence EGYR showed closest correlation with diagnosis and was selected for further evaluation (FIG. 1).

Example 2: LARP1 in Plasma Collected from Mouse Xenografts

Immune competent syngeneic mice were inoculated with ovarian cancer cells and a blood draw was obtained at 4 weeks. Plasma samples were prepared for mass spectroscopy and analysed using methods described above. All peptides were well separated with the retention times for the peptide as follows, 6.3, 10.5, 4.5, 12.5, 9.4, 8.6 and 9.1 min, for peptide sequences 1-7, respectively. The limit of quantification (LOQ) was 1 ng/ml. Linearity of the calibration curve was determined by plotting peak area ratio of each peptide sequence to corresponding labelled internal standard against the peptide concentrations. A linear response was obtained for all peptides ($r^2$>0.994). FIG. 1A shows typical calibration curve for a LARP1 peptide sequence. Typical chromatograms showing LARP1 peptide sequence to be detectable only in calibration standards (FIG. 1B), and inoculated ovarian tumour mice (FIG. 1D) but not in the untreated mice plasma (FIG. 1C). The average recovery in spiked plasma samples was 82.1±10.4%. Within-day imprecision was <9% and between-day imprecision <14%. Inaccuracy was within 15% of the nominal values for the spiked controls.

FIG. 2 shows the quantification of LARP1 in mouse plasma as measured by the average concentration of the 7 LARP1 specific peptide sequences. LARP1 was found to be absent in untreated mice. Whereas in the mice inoculated with 5×10$^6$ of ovarian tumor cells, LARP1 concentrations were detectable in week 2, 4, 5 and 6 after inoculation. LARP1 concentrations varied between 40.1-121.5 ng/ml with maximum concentration detected at week 4 (FIG. 2A). LARP1 expression in the inoculated mice was confirmed in peritoneum and omentum using immunohistochemistry (FIG. 2B). LARP1 concentrations normalized to the expected number of inoculated cells at each week was found to range between 3.6-11.7 femtog/single cell (ng/million cells) (FIG. 2C).

Example 3: LARP1 from the Serum of Women Ovarian Masses, Ovarian Cancer and Age-Matched Controls Serum (note, not plasma) was collected from 232 women aged over 50 years who participated in an ovarian cancer study. Of these, 50 had benign ovarian masses, 126 had ovarian cancer, 6 had endometriosis and 50 age-matched controls, LARP1 was measured using similar methodology to that described above, using the tetrapeptide EGYR and normalised to labelled EGYR. Higher levels of LARP1 were observed in women with a diagnosis of ovarian cancer compared to non-cancer diagnosis or controls. In terms of 5 year survival, on a ROC curve LARP1 showed a sensitivity (AUC) of 0.706 compared to CA125 with AUC of 0.941. From this, we conclude that levels of serum LARP1 (measured in serum and compared to circulating CA125 levels) are higher in patients with cancer and, within cancer cases, correlate with worse survival outcome.

Experiment 4: Plasma LARP1 in Women with Hereditary Cancer Risk

Plasma was collected from 35 women known to carry BRCA1, BRCA2 or other germ-line genetic mutations associated with enhanced risk of breast or ovarian cancer. Samples were taken prior to women undergoing risk-reducing bilateral salpingo-oophorectomy (RRBSO). LARP1 was measured using the EGYR tetrapeptide with methodology as described above. In 30 of these women, levels of LARP1 measured 25 ug/ml or lower and histological reports from RRBSO showed no abnormalities, apart from one woman with a focus of STIL identified within one fallopian tube. Of the 5 women with levels of LARP1 over 25 ug/ml, one had a concurrent diagnosis of non-Hodgkin lymphoma, one had a Brenner cancer in their ovary, one had no abnormal or concurrent findings, one had a focus of STIL that was 100% LARP1 positive (on tissue staining) and one had normal histology but awaits risk-reducing mastectomy. These findings indicate that plasma LARP1 with a cutoff value of approximately 25 ug/ml may be a marker of preinvasive cancer.

The summary of the invention described above is non-limiting and other features and advantages of the invention will be apparent from the following detailed description of the invention, and from the claims.

The invention claimed is:

1. A method for detecting LARP-1 protein in a biological sample, comprising producing a protein digest from the biological sample; and detecting for the presence of EGYR fragment peptide in the protein digest, thereby determining the presence of LARP-1 in the biological sample.

2. The method of claim 1, wherein the protein digest comprises a serine-protease digest.

3. The method of claim 2, wherein the serine-protease digest comprises a trypsin digest.

4. The method of claim 1, wherein the proteins in the sample are reduced and alkylated.

5. The method of claim 1, wherein the detecting comprises mass spectrometry (MS).

6. The method of claim 5, wherein the EGYR peptide is fragmented in tandem mass spectrometry (MS: MS) mode and a fragment of EGYR with m/z of 136.1 in positive ion mode ionisation is detected.

7. The method of claim 1, wherein the detecting comprises liquid chromatography (LC) and MS.

8. The method of claim 1, wherein the biological sample is selected from the group consisting of: a blood sample, a plasma sample, a serum sample, a urine sample, an ascites sample and a saliva sample.

9. The method of claim 1, wherein the biological sample is from a patient with or suspected of having cancer or pre-cancer.

10. The method of claim 9, wherein the cancer is selected from the group consisting of: ovarian cancer, breast cancer, pancreatic cancer, colon cancer and hepatocellular cancer.

11. The method of any of claim 9, wherein the patient possesses germline BRCA1 or BRCA-2 mutations or other cancer-predisposing mutations/syndromes.

12. The method of claim 1, further comprising further quantifying the EGYR fragment peptide.

13. The method of claim 12, wherein quantifying the EGYR fragment peptide comprises comparing the amount of detected peptide to an EGYR peptide standard of known amount, wherein the EGYR peptide standard is isotopically labelled.

14. A method of predicting the presence of serous tubal intraepithelial carcinoma (STIC) in a subject comprising detecting the level of LARP1 protein in a serum or plasma sample from the subject; and comparing the level of LARP1 protein in said sample with a reference value of LARP1 protein or with the level of LARP1 in a control sample, wherein an elevated level of LARP1 protein in said sample from said subject compared to the reference value or the level of LARP1 protein in the control sample predicts that the subject has STIC; wherein the level of LARP1 protein is quantified by detecting the level of LARP1-derived EGYR peptide.

15. A method for diagnosing or predicting risk of developing cancer, the method comprising:
subjecting a biological sample obtained from a patient to one or more processing steps to cleave the proteins in the sample into smaller peptides, wherein if LARP1 protein is in the sample the peptides produced include EGYR peptide;
subjecting the processed sample to ionization under conditions suitable to produce one or more multiply charged ions detectable by mass spectrometry;
determining by mass spectrometry the amount of one or more ions from the LARP1-derived EGYR peptide; and
using the determined ion amounts to determine the amount of LARP1 protein in the biological sample or EGYR peptide in the processed sample, wherein an elevated LARP1 protein level in the biological sample relative to normal indicates the presence of or risk of developing cancer.

16. The method according to claim 15, wherein the patient comprises cancer-predisposing mutations in its genomic DNA.

17. The method according to claim 16, wherein the patient possesses germline BRCA1 or BRCA-2 mutations.

18. The method according to claim 16, wherein the patient comprises germline driving mutations in a gene selected from: BRCA1, BRCA2, KRAS, P53, ALK and HER2.

19. The method according to claim 15, wherein the patient has a syndrome selected from BRCA, Lynch and Li Fraumen.

20. A peptide standard for quantifying LARP-1 in a biological sample, comprising an amino acid sequence EGYR, wherein said peptide standard is utilized in the method of claim 1.

21. The peptide standard of claim 20, wherein the arginine amino acid in the EGYR peptide is labelled with an isotope containing four 15N and six 13C, leading to a mass shift of +10 Da.

22. The method according to claim 14, wherein the subject comprises cancer-predisposing mutations in its genomic DNA.

23. The method according to claim 22, wherein the patient possesses germline BRCA1 or BRCA-2 mutations.

24. The method according to claim 22, wherein the patient comprises germline driving mutations in a gene selected from: BRCA1, BRCA2, KRAS, P53, ALK and HER2.

* * * * *

SEQUENCE LISTING

<160> NUMBER OF SEQ ID NOS: 9

<210> SEQ ID NO 1
<211> LENGTH: 6652
<212> TYPE: DNA
<213> ORGANISM: Homo sapiens

<400> SEQUENCE: 1

| | | | | | |
|---|---|---|---|---|---|
| gccagagcca | ggaggcagct | gtgcgatctg | gatgtaccta | aaccctccag | ggccacatag | 60 |
| tgacccagg | ccctggtcac | tccatgcttt | ggagggtgct | tttgtcaaag | aggcctcctt | 120 |
| tccctcaccc | agagctggat | ttccaagagg | ctcccatacc | tagctgccct | ggcagactcc | 180 |
| cagggaggaa | aaacagcgtg | gccttggcag | ctgccccgag | gaaggagccc | acaggtgaca | 240 |
| gggagaagcc | attgccattc | cctgtcctgg | ccccctcag | caaccctgaa | cactctgctc | 300 |
| cagccaaggt | ggtgagggca | gctgttccta | aacagcgcaa | aggcagcaag | gttggtgact | 360 |
| ttggagatgc | aatcaattgg | cccacacctg | agagatagc | ccacaagagt | gttcagccac | 420 |
| agtcccacaa | gcctcagcct | acccgtaaac | tgccacccaa | gaaggacatg | aaggaacagg | 480 |
| agaaaggaga | agggagtgat | agtaaggaga | gtccaaaaac | caaatcagat | gaatcagggg | 540 |
| aggaaaagaa | tggagatgag | gattgccagc | gaggcgggca | gaagaagaaa | ggaaacaaac | 600 |
| acaagtgggt | tccattacaa | atagacatga | agcctgaagt | gcccagagag | aaactggctt | 660 |
| cacgccccac | tcgcccaccg | gagcctagac | acatacctgc | caatcgcgga | gagatcaaag | 720 |
| ggtctgagtc | tgccacctac | gtgcccgtgg | cccccccac | cccagcctgg | caaccagaga | 780 |
| tcaaaccgga | gcctgcctgg | cacgaccagg | atgagacatc | gagtgtgaag | agtgatgggg | 840 |
| ctggtggggc | gcgggcttcc | ttccgtggcc | gtggacgggg | gcgtggtcgc | ggccgggac | 900 |
| gcggccgggg | tggcactcga | acccattttg | actaccagtt | tggctaccga | aagtttgatg | 960 |
| gtgtggaggg | gcctcgtacg | cccaagtaca | tgaacaacat | cacctactac | tttgacaatg | 1020 |
| tcagcagcac | cgagctttac | agtgtggatc | aggaactgct | caaagactac | atcaagcgcc | 1080 |
| agattgaata | ctacttcagc | gtggacaatt | tagagcgaga | cttcttcctg | cgaaggaaaa | 1140 |
| tggatgctga | tggtttccta | cccatcaccc | ttattgcttc | cttccaccga | gtgcaggccc | 1200 |
| ttaccactga | catttcactc | atctttgcgg | ccctaaagga | cagcaaggtg | gtggagatcg | 1260 |
| ttgatgagaa | agttcgtagg | agggaggaac | cagaaaagtg | gcctcttccc | ccaatagtgg | 1320 |
| attattcaca | gactgatttc | tcccagcttc | tcaactgccc | tgaatttgtt | ccccgtcagc | 1380 |
| actaccaaaa | ggagacagag | tcggcacctg | gctctcctcg | tgcagtcacc | ccagtgccaa | 1440 |
| ccaaaacaga | ggaggtcagc | aacctaaaga | cactacccaa | gggcctgtct | gccagcctgc | 1500 |
| ctgacctgga | ttctgagaac | tggattgaag | tgaagaagag | gcctcggcca | tccccagcac | 1560 |
| ggcccaagaa | gtcagaggag | tccagatttt | cccacctgac | ctctctgcct | cagcagctgc | 1620 |
| cttcccagca | gctgatgtcc | aaggatcagg | atgagcaaga | ggaactggat | tttctgtttg | 1680 |
| acgaggagat | ggagcagatg | gatgggcgga | agaacacctt | cactgcctgg | tctgatgagg | 1740 |
| aatctgacta | tgagattgat | gacagggatg | tcaacaagat | cctcattgtc | acccagacac | 1800 |
| cacattacat | gcgccggcac | ccagggggg | accgcacagg | caaccacacc | tcgcgtgcca | 1860 |
| agatgagcgc | cgaactggcc | aaggtcatta | atgatggcct | cttctactat | gagcaggacc | 1920 |
| tgtgggctga | aaagtttgaa | cctgagtatt | cccagatcaa | gcaagaagtc | gagaacttca | 1980 |
| aaaaggtcaa | tatgatcagc | cgggagcagt | ttgcacact | gaccctgag | ccccctgtgg | 2040 |
| atcccaacca | ggaagttcct | cctgggccac | ctcggttcca | gcaagttcct | acggatgccc | 2100 |

```
tggccaacaa gttgtttggt gctcctgagc cctccaccat cgcccgctct ctaccaacca    2160
ctgtcccaga gtcaccaaac taccgcaaca ccaggacccc tcgcactccc cggacaccac    2220
agctcaaaga ctcaagccag acatcacggt tttacccagt ggtgaaagaa ggacggacac    2280
tggatgccaa gatgcctcga aaagaaaga caagacacag ttcaaaccca cccttggaga     2340
gccatgtggg ctgggtgatg gattcccgtg agcacaggcc ccgtactgct tccatcagct    2400
ccagcccctc agaagggacg cctacagttg cagctatgg ctgtacccct cagtcattgc     2460
ccaagttcca gcatccttcc catgaactgc tcaaggaaaa tggcttcaca caacacgtct    2520
accataagta tcgtaggcgc tgccttaatg agcggaaacg cttgggcatt ggccagtctc    2580
aggagatgaa cacactcttc cgcttctggt ccttcttcct ccgagatcac ttcaacaaaa    2640
agatgtatga ggagttcaag cagctggctc tggaggacgc caagaaggc tacagatatg     2700 gtttggagtg cctttttcga tactacagtt atggcctgga aaagaagttc cggctggaca    2760
tattcaagga ttttcaggag gaaacggtga aggactatga agctggccaa ctgtatgggc    2820
tggagaagtt ctgggccttc ttgaaatatt ccaaagccaa aaatttggac attgaccccca   2880 aactgcaaga ataccctcggc aaattccgac gtcttgaaga cttccgagta gatcccccca    2940
tgggtgagga gggcaaccac aagcgacact cagtggtagc aggaggtggc ggcggtgagg    3000
gcaggaagcg gtgcccctcc cagtcttcca gcaggcctgc tgccatgatc agccaacccc    3060
ctacaccacc caccggccag cctgtccggg aagatgccaa atggacaagc cagcactcga    3120
acacacagac tttgggaaag tgaaaagctc cttagccctg gggcttgagg ggggaaaggg    3180
gtagggtggg taagagtcca tgggggtgcc cagtcccagg agaggggaca atgaagggac    3240
aggcctggag ttactaggac aggcctttgt gctgagtagc aatgtataca ccatttgggc    3300
tatcagaggt acccctgggc aggagcctct acatcccctt cccccctcctc tctccatgac   3360 tcttgacatc ctagcttctt ctaaggggg agggaagg gggagatttt tatatatata       3420
tacatatata tatatcaagt tttaaattat tgatagttca tctggattac caaaatcact    3480
ctgcagccct gcccgaggct agtaggctgc aaccctggtc cccaccccta acctcctgct    3540
ccccctcaag ccaactatgc agcccacaag aaggccctgc gggcccccccc attgcccagc   3600 actgtctcat agaaggctct ggtggtacct ctgggcccca ggagcatcag cccccttgatc   3660 atctgggttt tgtcatcacc atattttctc cctgctgttc ccaccatgcc cttctgccat    3720
cttctgggag aaggaaacca aaggatctaa aactggggtt tgggggaagg tttcagcctc    3780
tccccactcc ccttgcccca ccccttttac tccccagccc agagagacgc tgcttttacc    3840
aggaaagact attgaaagat gttttatttt attttctct gacctttcca tccttgaaaa     3900 aatgggaaa aagaagaaa aaagacaaaa tcgaccataa aagaccaaaa aaaaaaaaa       3960 aatcagaaaa cccccaccta atccacagaa agtaatgtct ttcccctccc cttggaattt    4020
ttgttttgtt tttggaaata atattttttt aaaagttgcc ttattgtgga gcggaatct     4080 gaaatacca aatgcctgtt ttcctcggtg gagtcaaccc gaagagctcc caccttctct     4140
ggatgtgcct gggcttggac tggctagaat cttttctctgg actgttgcat gtacagtgcc   4200
tccatcctgg aggcaagaga gttggagtg gctcgaatca gagccgtgcc caagatatcc     4260
ctgctgttgc atcgtttgaa gctgacgtcc tgtgtctgta cactgctgcc actgttgtgt    4320
cctcgctctg cttgctgttg cctcacgcca ggccccgtcc tgccgtgaca cccttcatcc    4380 taccccttgga accccaaggc caagttggtt caaactgttg gagaacagag ttggcctgca   4440
```

```
tctgaacac acttgtcctc agcttaccat ctcctcacac cccagagtgg aaaggtgaac    4500
acctgcagct gaggcttgga aacgtttctt gtgttgccct gaaaaatctt tgagacctca    4560
gggaggctct gtctctctta aaaggtggag aaagatgcca ttctctccct aaggtctggt    4620
ggagtctccc catcttgcat acccttctgc aagccatcta tctctgctca ctctccaatt    4680
gacccgcctg ggaacaaggg atgaggagga gttgggggct gggggggaatc ctgccagttg    4740 gtgaagccct gtggcaggaa ggtatatgtg gacatagagt ataccctgatt ctctttcttc    4800 agccactgac tgcttgggtt gggctgtgaa tgataatgga atggctggag tctgctgttg    4860
tcagaaggca gggagggtga tgaaggactg acccacatgg actgggatgt gtgtcggtta    4920
tgggcatgac tgcacgttca ctctcagtgg gatctgggca acatggagtt cattgtcctg    4980
ttgcttactt actgcaatgt ctttggcccc tcttttcaac tggttcctct gttgggccca    5040
aaggttggga gtaggagaca gtatcccagg ctgacaaggg cttgcccttt accttgggca    5100
ccttgttaat ttttagcctg tgcccttccc caccttgcc ctcccagtgg ttggtatgtg    5160
ggaagcccat ctcagttcct gtgacttcat gtctcaaacc aaggatgagc gtctggtctc    5220
tgctatgatg gtggtatccg aggcctttcc ctgcccagtc tggtgcctgc cccacattgt    5280
accggacact ggattcctgg accccctttct cctttccttt ctttccttca ggtcacgcag    5340
ccctgtactg tatccagcac cacagaaacc tcagtgtttt tcctctgctg gtttggggca    5400
caaggaagcc ttagggtatg gggaaaggct gttattacct agagtttact cccaggccag    5460
ggggctgcca tcttcttcac agacatccct gaaaggaagc ccctttgggg cagggaggtg    5520
aggacttcat ctcaacatcg gctggtggtt ggtaggggag ctttttcttt tctttccttt    5580 tttttttgttt ttgttttgt ttttgttttt ggtaacatgt taggagttaa tgttgcaaag    5640
agtagtttac atcttcactt tctgaagaca cttgaattta ggaccgatgt atctgtgaca    5700
agcatgccag aagtggcagg ggccatcagg gctaaccact tcacacctac catcgtccca    5760 tgggatcca agacctgaga taaagcaaca gcctgcccag atccctctgt tcatcctatc    5820
ccttccaagg ttggtccatg ccaacataac ctctgggcat cagacatcag caggtctgtg    5880
tgcctcagcc ctgttaaggg gcaggtttct ctttagcccc cttcctgcac ttgggagcaa    5940
aggcactacc agtagagaag ggccatccag ccgtgcccca gcctggaccc ctggggctca    6000
gatagaggtg ctgagcccct gtgtcaaagt tgttaaatgt ttttgttttg ttccattgta    6060
gctctttttt ttttttttc ccctttcctg gtgattgatt ttacaaaaga aagtaagctg    6120
cttagaaggc cctggaaggg aagtgaggag gagggacaag gaagatgact agttacggag    6180
ggtgagggtt gttttttgcc aaaaagcctg ggtagagtga tctgaattat ctggcaccct    6240
cctgaatgga accccagagt acctcctgtg tggaagggtc cctggatttt ccctaacacc    6300
caccctctcc cccttcagcc atgctgatgg cagagaagat aagaacttgg agcccatttc    6360
tcactggaga ggaaaacttg tcatctggct ttgcggagaa ggttccacct tacgctcgta    6420
gtacattatc tttactatgt gctaggatat catatttaaa aggacaaaaa aatgtaaaat    6480
acttgaatga gcttgtatta taacattaat attattgaga gtatctgctt tccaggctga    6540
agtgattcat tcattattct agtcctgctt tagtcctttg taatttgtgg taattatgct    6600
tttcttttta atacaaaaaa atgtatataaa ataaacactt gaaaaggcaa aa    6652
```

<210> SEQ ID NO 2
<211> LENGTH: 1019
<212> TYPE: PRT
<213> ORGANISM: Homo sapiens

<400> SEQUENCE: 2

```
Met Leu Trp Arg Val Leu Leu Ser Lys Arg Pro Pro Phe Pro His Pro
1               5                   10                  15

Glu Leu Asp Phe Gln Glu Ala Pro Ile Pro Ser Cys Pro Gly Arg Leu
            20                  25                  30

Pro Gly Arg Lys Asn Ser Val Ala Leu Ala Ala Pro Arg Lys Glu
        35                  40                  45

Pro Thr Gly Asp Arg Glu Lys Pro Leu Pro Phe Pro Val Leu Ala Pro
    50                  55                  60

Phe Ser Asn Pro Glu His Ser Ala Pro Ala Lys Val Val Arg Ala Ala
65                  70                  75                  80

Val Pro Lys Gln Arg Lys Gly Ser Lys Val Gly Asp Phe Gly Asp Ala
                85                  90                  95

Ile Asn Trp Pro Thr Pro Gly Glu Ile Ala His Lys Ser Val Gln Pro
                100                 105                 110

Gln Ser His Lys Pro Gln Pro Thr Arg Lys Leu Pro Pro Lys Lys Asp
            115                 120                 125

Met Lys Glu Gln Glu Lys Gly Glu Gly Ser Asp Ser Lys Glu Ser Pro
130                 135                 140

Lys Thr Lys Ser Asp Glu Ser Gly Glu Glu Lys Asn Gly Asp Glu Asp
145                 150                 155                 160

Cys Gln Arg Gly Gly Gln Lys Lys Lys Gly Asn Lys His Lys Trp Val
                165                 170                 175

Pro Leu Gln Ile Asp Met Lys Pro Glu Val Pro Arg Glu Lys Leu Ala
            180                 185                 190

Ser Arg Pro Thr Arg Pro Pro Glu Pro Arg His Ile Pro Ala Asn Arg
        195                 200                 205

Gly Glu Ile Lys Gly Ser Glu Ser Ala Thr Tyr Val Pro Val Ala Pro
    210                 215                 220

Pro Thr Pro Ala Trp Gln Pro Glu Ile Lys Pro Glu Pro Ala Trp His
225                 230                 235                 240

Asp Gln Asp Glu Thr Ser Ser Val Lys Ser Asp Gly Ala Gly Gly Ala
            245                 250                 255

Arg Ala Ser Phe Arg Gly Arg Gly Arg Gly Arg Gly Arg Gly
        260                 265                 270

Arg Gly Arg Gly Gly Thr Arg Thr His Phe Asp Tyr Gln Phe Gly Tyr
    275                 280                 285

Arg Lys Phe Asp Gly Val Glu Gly Pro Arg Thr Pro Lys Tyr Met Asn
290                 295                 300

Asn Ile Thr Tyr Tyr Phe Asp Asn Val Ser Ser Thr Glu Leu Tyr Ser
305                 310                 315                 320

Val Asp Gln Glu Leu Leu Lys Asp Tyr Ile Lys Arg Gln Ile Glu Tyr
            325                 330                 335

Tyr Phe Ser Val Asp Asn Leu Glu Arg Asp Phe Phe Leu Arg Arg Lys
        340                 345                 350

Met Asp Ala Asp Gly Phe Leu Pro Ile Thr Leu Ile Ala Ser Phe His
    355                 360                 365

Arg Val Gln Ala Leu Thr Thr Asp Ile Ser Leu Ile Phe Ala Ala Leu
    370                 375                 380

Lys Asp Ser Lys Val Val Glu Ile Val Asp Glu Lys Val Arg Arg Arg
385                 390                 395                 400

Glu Glu Pro Glu Lys Trp Pro Leu Pro Pro Ile Val Asp Tyr Ser Gln
```

```
                405                 410                 415
Thr Asp Phe Ser Gln Leu Leu Asn Cys Pro Glu Phe Val Pro Arg Gln
            420                 425                 430
His Tyr Gln Lys Glu Thr Glu Ser Ala Pro Gly Ser Pro Arg Ala Val
            435                 440                 445
Thr Pro Val Pro Thr Lys Thr Glu Glu Val Ser Asn Leu Lys Thr Leu
450                 455                 460
Pro Lys Gly Leu Ser Ala Ser Leu Pro Asp Leu Asp Ser Glu Asn Trp
465                 470                 475                 480
Ile Glu Val Lys Lys Arg Pro Arg Pro Ser Pro Ala Arg Pro Lys Lys
            485                 490                 495
Ser Glu Glu Ser Arg Phe Ser His Leu Thr Ser Leu Pro Gln Gln Leu
            500                 505                 510
Pro Ser Gln Gln Leu Met Ser Lys Asp Gln Asp Glu Gln Glu Glu Leu
            515                 520                 525
Asp Phe Leu Phe Asp Glu Glu Met Glu Gln Met Asp Gly Arg Lys Asn
            530                 535                 540
Thr Phe Thr Ala Trp Ser Asp Glu Glu Ser Asp Tyr Glu Ile Asp Asp
545                 550                 555                 560
Arg Asp Val Asn Lys Ile Leu Ile Val Thr Gln Thr Pro His Tyr Met
                565                 570                 575
Arg Arg His Pro Gly Gly Asp Arg Thr Gly Asn His Thr Ser Arg Ala
            580                 585                 590
Lys Met Ser Ala Glu Leu Ala Lys Val Ile Asn Asp Gly Leu Phe Tyr
            595                 600                 605
Tyr Glu Gln Asp Leu Trp Ala Glu Lys Phe Glu Pro Glu Tyr Ser Gln
            610                 615                 620
Ile Lys Gln Glu Val Glu Asn Phe Lys Lys Val Asn Met Ile Ser Arg
625                 630                 635                 640
Glu Gln Phe Asp Thr Leu Thr Pro Glu Pro Pro Val Asp Pro Asn Gln
                645                 650                 655
Glu Val Pro Pro Gly Pro Arg Phe Gln Gln Val Pro Thr Asp Ala
            660                 665                 670
Leu Ala Asn Lys Leu Phe Gly Ala Pro Glu Pro Ser Thr Ile Ala Arg
            675                 680                 685
Ser Leu Pro Thr Thr Val Pro Glu Ser Pro Asn Tyr Arg Asn Thr Arg
            690                 695                 700
Thr Pro Arg Thr Pro Arg Thr Pro Gln Leu Lys Asp Ser Ser Gln Thr
705                 710                 715                 720
Ser Arg Phe Tyr Pro Val Val Lys Glu Gly Arg Thr Leu Asp Ala Lys
                725                 730                 735
Met Pro Arg Lys Arg Lys Thr Arg His Ser Ser Asn Pro Pro Leu Glu
            740                 745                 750
Ser His Val Gly Trp Val Met Asp Ser Arg Glu His Arg Pro Arg Thr
            755                 760                 765
Ala Ser Ile Ser Ser Ser Pro Ser Glu Gly Thr Pro Thr Val Gly Ser
            770                 775                 780
Tyr Gly Cys Thr Pro Gln Ser Leu Pro Lys Phe Gln His Pro Ser His
785                 790                 795                 800
Glu Leu Leu Lys Glu Asn Gly Phe Thr Gln His Val Tyr His Lys Tyr
                805                 810                 815
Arg Arg Arg Cys Leu Asn Glu Arg Lys Arg Leu Gly Ile Gly Gln Ser
            820                 825                 830
```

```
Gln Glu Met Asn Thr Leu Phe Arg Phe Trp Ser Phe Leu Arg Asp
        835                 840                 845

His Phe Asn Lys Lys Met Tyr Glu Glu Phe Lys Gln Leu Ala Leu Glu
    850                 855                 860

Asp Ala Lys Glu Gly Tyr Arg Tyr Gly Leu Glu Cys Leu Phe Arg Tyr
865                 870                 875                 880

Tyr Ser Tyr Gly Leu Glu Lys Lys Phe Arg Leu Asp Ile Phe Lys Asp
                885                 890                 895

Phe Gln Glu Glu Thr Val Lys Asp Tyr Glu Ala Gly Gln Leu Tyr Gly
            900                 905                 910

Leu Glu Lys Phe Trp Ala Phe Leu Lys Tyr Ser Lys Ala Lys Asn Leu
        915                 920                 925

Asp Ile Asp Pro Lys Leu Gln Glu Tyr Leu Gly Lys Phe Arg Arg Leu
    930                 935                 940

Glu Asp Phe Arg Val Asp Pro Pro Met Gly Glu Gly Asn His Lys
945                 950                 955                 960

Arg His Ser Val Val Ala Gly Gly Gly Gly Glu Gly Arg Lys Arg
                965                 970                 975

Cys Pro Ser Gln Ser Ser Arg Pro Ala Ala Met Ile Ser Gln Pro
            980                 985                 990

Pro Thr Pro Pro Thr Gly Gln Pro  Val Arg Glu Asp Ala  Lys Trp Thr
        995                 1000                1005

Ser Gln  His Ser Asn Thr Gln  Thr Leu Gly Lys
    1010                1015

<210> SEQ ID NO 3
<211> LENGTH: 4
<212> TYPE: PRT
<213> ORGANISM: Homo sapiens

<400> SEQUENCE: 3

Glu Gly Tyr Arg
1

<210> SEQ ID NO 4
<211> LENGTH: 5
<212> TYPE: PRT
<213> ORGANISM: Homo sapiens

<400> SEQUENCE: 4

Leu Asp Ile Phe Lys
1               5

<210> SEQ ID NO 5
<211> LENGTH: 5
<212> TYPE: PRT
<213> ORGANISM: Homo sapiens

<400> SEQUENCE: 5

Asp His Phe Asn Lys
1               5

<210> SEQ ID NO 6
<211> LENGTH: 6
<212> TYPE: PRT
<213> ORGANISM: Homo sapiens

<400> SEQUENCE: 6

Phe Trp Ala Phe Leu Lys
```

```
<210> SEQ ID NO 7
<211> LENGTH: 7
<212> TYPE: PRT
<213> ORGANISM: Homo sapiens

<400> SEQUENCE: 7

Asn Leu Asp Ile Asp Pro Lys
1               5

<210> SEQ ID NO 8
<211> LENGTH: 6
<212> TYPE: PRT
<213> ORGANISM: Homo sapiens

<400> SEQUENCE: 8

Arg Leu Glu Asp Phe Arg
1               5

<210> SEQ ID NO 9
<211> LENGTH: 7
<212> TYPE: PRT
<213> ORGANISM: Homo sapiens

<400> SEQUENCE: 9

Leu Gln Glu Tyr Leu Gly Lys
1               5
```